US009442525B2

(12) United States Patent
Choi et al.

(10) Patent No.: US 9,442,525 B2
(45) Date of Patent: Sep. 13, 2016

(54) WEARABLE DEVICES

(71) Applicant: Samsung Electronics Co., Ltd., Gyeonggi-do (KR)

(72) Inventors: Jongmin Choi, Gyeonggi-do (KR); Hongmoon Chun, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 23 days.

(21) Appl. No.: 14/617,004

(22) Filed: Feb. 9, 2015

(65) Prior Publication Data

US 2015/0241916 A1   Aug. 27, 2015

(30) Foreign Application Priority Data

Feb. 21, 2014  (KR) .................. 10-2014-0020580

(51) Int. Cl.
| | |
|---|---|
| G06F 1/16 | (2006.01) |
| A61B 5/00 | (2006.01) |
| G04G 21/02 | (2010.01) |
| A61B 5/0205 | (2006.01) |
| G04G 21/00 | (2010.01) |
| A61B 5/11 | (2006.01) |

(52) U.S. Cl.
CPC ............ *G06F 1/163* (2013.01); *A61B 5/0205* (2013.01); *A61B 5/1118* (2013.01); *A61B 5/681* (2013.01); *G04G 21/00* (2013.01); *G04G 21/025* (2013.01); *A61B 5/1112* (2013.01)

(58) Field of Classification Search
CPC ... H04N 5/23206; G06F 1/26; G06F 1/1616; H04B 1/38
USPC ............... 455/575.6, 558, 90.3, 405, 407; 345/597, 694, 590, 691, 173, 625, 633; 348/148, 14.08, 158; 361/679.3, 361/679.03, 679.52, 679.26
See application file for complete search history.

(56) References Cited

U.S. PATENT DOCUMENTS

| | | |
|---|---|---|
| 8,170,633 B2 | 5/2012 | Shin et al. |
| 8,568,313 B2 | 10/2013 | Sadhu |
| 2003/0065257 A1 | 4/2003 | Mault et al. |
| 2010/0112964 A1 | 5/2010 | Yi et al. |

(Continued)

FOREIGN PATENT DOCUMENTS

| | | |
|---|---|---|
| KR | 20-0439498 Y1 | 4/2008 |
| KR | 10-2009-0046306 A | 5/2009 |

(Continued)

OTHER PUBLICATIONS

"LG GD910 User Guide"; Oct. 8, 2009; XP055195985.
Blog, [IFA2013 Detailed Analysis], Galaxy Gear, a Big Stain rather than a Mark? Posted in Review/IFA 2013 by Boongeo IQ, Sep. 6, 2013, pp. 1-13.

(Continued)

*Primary Examiner* — Hung Duong
(74) *Attorney, Agent, or Firm* — Cha & Reiter, LLC

(57) ABSTRACT

Wearable devices are provided. The wearable device may include a body enclosed by: a front shaped as a rounded square or a rounded rectangle; a back opposite to the front; and an upper side, a lower side, a left side and a right side, which couple the front and back and are between the front and back. The wearable device may also includes: an upper band coupled to the upper side; a lower band coupled to the lower side; a display placed on the front of the body; a camera module disposed on the upper side; and a key disposed on the lower side, the key being operated by being pressed.

24 Claims, 22 Drawing Sheets

(56) References Cited

U.S. PATENT DOCUMENTS

| | | |
|---|---|---|
| 2011/0012796 A1 | 1/2011 | Kim et al. |
| 2011/0157046 A1 | 6/2011 | Lee et al. |
| 2013/0146659 A1 | 6/2013 | Zhou et al. |
| 2013/0329532 A1* | 12/2013 | Sorias .................. G04C 10/00 368/64 |
| 2015/0265034 A1* | 9/2015 | Lee ......................... A45F 5/00 224/219 |
| 2016/0025766 A1* | 1/2016 | Hong .................. G01C 22/006 702/141 |
| 2016/0065831 A1* | 3/2016 | Howard ............. H04N 5/23206 348/211.2 |

FOREIGN PATENT DOCUMENTS

| | | |
|---|---|---|
| KR | 10-2010-0048273 A | 5/2010 |
| KR | 10-2010-0050028 A | 5/2010 |
| KR | 10-2011-0006999 A | 1/2011 |
| KR | 10-2011-0078008 A | 7/2011 |
| WO | 2010/005406 A1 | 1/2010 |

OTHER PUBLICATIONS

Column, "Nissan, Adidas, . . . " Smartwatch, Breaking the Boundaries, Columnist Meang Sung Hyun, Oct. 21, 2013, pp. 1-22.
Korean Search Report dated Jun. 29, 2016.

* cited by examiner

WEARABLE DEVICES

CLAIM OF PRIORITY

This application claims the benefit under 35 U.S.C. §119 (a) of a Korean patent application filed on Feb. 21, 2014 in the Korean Intellectual Property Office and assigned Serial No. 10-2014-0020580, the entire disclosure of which is hereby incorporated by reference.

BACKGROUND

1. Technical Field

The present disclosure generally relates to wearable devices that are worn on the human body, e.g., on a person's wrist, arm, etc.

2. Description of the Related Art

In general, electronic devices, such as smart phones, tablet PCs, Portable Multimedia Players (PMPs), Personal Digital Assistants (PDAs), laptop computers, etc., are designed to be hand-held and to have a form-factor that allows users to can carry them with one hand or in their pocket. Such devices are prone to being damaged or lost. For example, when carrying such a hand-held electronic device in one's hand, there is chance that the device will be dropped and damaged as a result. Also for example, When being carried in one's pocket, the device may slip out of the pocket and be lost. Such hand-held electronic devices are likely to be lost while users are carrying them or damaged by dropping.

SUMMARY

The present disclosure is generally directed to a wearable device that is worn on the human body, e.g., on a wrist, arm, etc. and may be equipped with a variety of functions.

In accordance with an exemplary embodiment of the present disclosure, a wearable device may include a body enclosed by: a front, a back opposite to the front, an upper side, a lower side, a left side, and a right side. The upper, lower, left, and right sides may couple the front and back. The front may be generally or substantially rectangular (e.g., a rectangle or a square) with rounded edges.

The wearable device may also include: an upper band coupled to the upper side; a lower band coupled to the lower side; a display placed on the front of the body; a camera module disclosed on the upper side; and a key, which may be operated by being pressed, disposed on the lower side.

In accordance with another exemplary embodiment of the present disclosure, a wearable device may include: a housing including a front, a back, a first side, a second side, a third side, and a fourth side. A wearable tool may be attached to part of the housing and worn on part of an object. A display may be included in the front. A camera window may be disposed on the first side, and an image sensor unit may be included inside the housing and located adjacent to the camera window. The front and the first side may form an obtuse angle.

These and other aspects of the present disclosure are described in greater detail hereinbelow.

BRIEF DESCRIPTION OF THE DRAWINGS

The features of the present disclosure will become more apparent from the following detailed description in conjunction with the accompanying drawings, in which.

DETAILED DESCRIPTION

Figure 1:
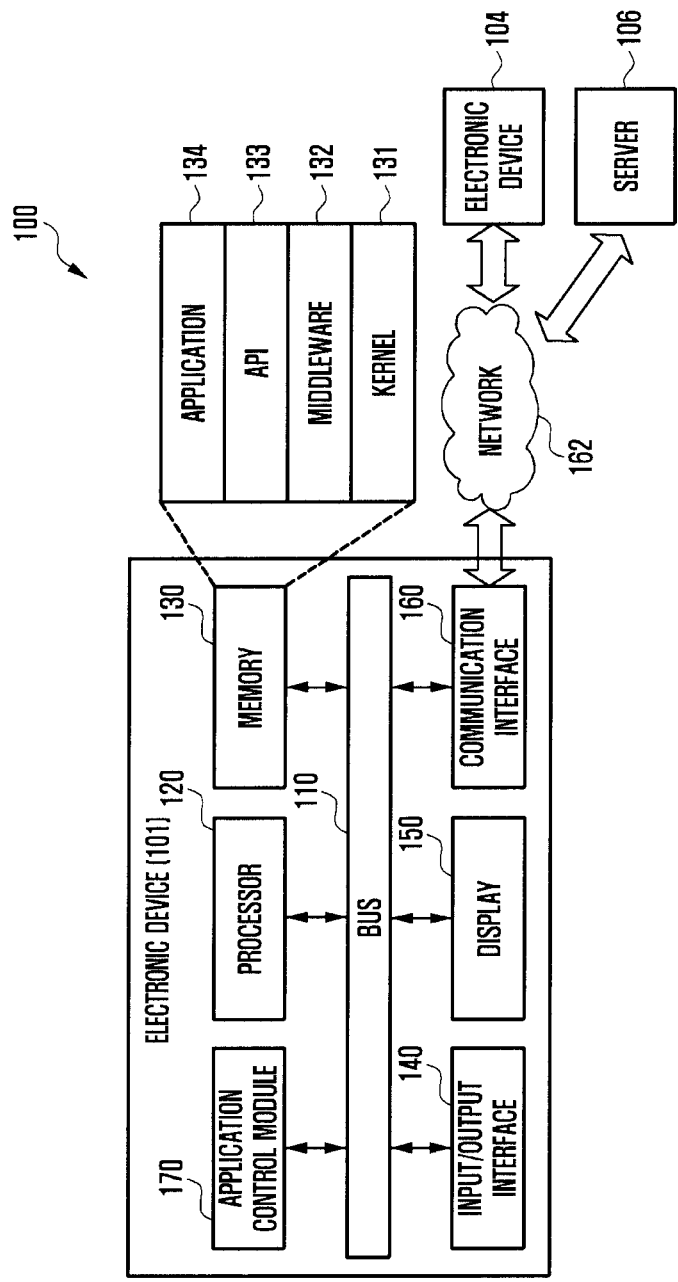
FIG. 1 illustrates a network environment including a wearable device according to an embodiment of the present disclosure.

Hereinafter, exemplary embodiments of the present disclosure are described in detail with reference to the accompanying drawings. The same reference numbers are used throughout the drawings to refer to the same or similar parts. For the purposes of clarity and simplicity, detailed descriptions of well-known functions and structures incorporated herein may be omitted to avoid obscuring the subject matter of the disclosure.

Although specific embodiments are illustrated in the drawings and related detailed descriptions are discussed in the present specification, the present disclosure may have various modifications and several embodiments. The various embodiments of the present disclosure are not limited to a specific implementation form and it should be understood that the present disclosure includes all changes and/or equivalents and substitutes included in the spirit and scope of the various embodiments of the present disclosure.

FIG. 1 illustrates a network environment 101 including a wearable device 100 according to an embodiment of the present disclosure. Referring to FIG. 1, the wearable device 100 may include a bus 110, a processor 120, a memory 130, an input/output interface 140, a display 150, a communication interface 160, and/or an application control module 170.

The bus 110 may be a circuit connecting the above-described components and transmitting communication (for example, a control message) between the above described components.

The processor 120 receives commands from other components (for example, the memory 130, the input/output interface 140, the display 150, the communication interface 160, or the application control module 170) through the bus 110, analyzes the received commands, and executes calculation or data processing according to the analyzed commands.

The memory 130 stores commands or data received from the processor 120 or other components (for example, the input/output interface 140, the display 150, the communication interface 160, or the application control module 170) or generated by the processor 120 or other components. The memory 130 may include programming modules, for example, a kernel 131, middleware 132, an Application Programming Interface (API) 133, and/or an application 134. Each of the aforementioned programming modules may be implemented by software, firmware, hardware, or a combination of two or more thereof.

The kernel 131 may control or manage system resources (for example, the bus 110, the processor 120, and/or the memory 130) used for executing an operation or function implemented by the remaining other programming modules, for example, the middleware 132, the API 133, or the application 134. Further, the kernel 131 may provide an interface for accessing individual components of the wearable device 100 from the middleware 132, the API 133, or the application 134 to control or manage the components.

The middleware 132 may perform a relay function of allowing the API 133 or the application 134 to communicate with the kernel 131 to exchange data. Further, in operation requests received from the application 134, the middleware 132 may perform a control for the operation requests (for example, scheduling or load balancing) by using a method of assigning a priority, by which system resources (for example, the bus 110, the processor 120, the memory 130 and the like) of the wearable device 100 can be used, to the application 134.

The API 133 is an interface by which the application 134 may control a function provided by the kernel 131 or the middleware 132 and may include, for example, at least one interface or function (for example, a command) for a file control, a window control, image processing, and/or a character control.

According to an exemplary embodiment, the application 134 may include a Short Message Service (SMS)/Multimedia Messaging Service (MMS) application, an email application, a calendar application, an alarm application, a health care application (for example, application measuring quantity of exercise or blood sugar) or an environment information application (for example, application providing information on barometric pressure, humidity or temperature). Additionally or alternatively, the application 134 may be an application related to an information exchange between the wearable device 100 and an external electronic device (for example, electronic device 104). The application related to the information exchange may include, for example, a notification relay application for transferring particular information to the external electronic device or a device management application for managing the external electronic device.

For example, the notification relay application may include a function of transmitting notification information generated by another application (for example, an SMS/MMS application, an email application, a health care application or an environment information application) of the wearable device 100 to the external electronic device (for example, electronic device 104). Additionally or alternatively, the notification relay application may receive notification information from, for example, the external electronic device 104 and may provide the received notification information to the user. The device management application may manage (for example, install, remove, or update) at least a part of functions (for example, turning on/off the external electronic device (or some components of the external electronic device) or controlling a brightness of the display) of the external electronic device (104 communicating with the electronic device 101, an application executed in the external electronic device 104, or a service (for example, call service or message service) provided by the external electronic device 104.

According to various embodiments, the application 134 may include an application designated according to an attribute (for example, type of electronic device) of the external electronic device 104. For example, when the external electronic device 104 is an MP3 player, the application 134 may include an application related to music reproduction. Similarly, when the external electronic device 104 is a mobile medical device, the application 134 may include an application related to health care. According to an embodiment, the application 134 may include at least one of an application designated to the wearable device 100 and an application received from an external electronic device (for example, server 106 or electronic device 104).

The input/output interface 140 may transmit a command or data input from the user through an input/output device (for example, a sensor, a keyboard, or a touch screen) to the processor 120, the memory 130, the communication interface 160, or the display control module 170 through, for example, the bus 110. For example, the input/output interface 140 may provide data on a user's touch input through a touch screen to the processor 120. Further, the input/output interface 140 may output a command or data received, through, for example, the bus 110, from the processor 120, the memory 130, the communication interface 160, or the application control module 170 through the input/output device (for example, a speaker or a display). For example, the input/output interface 140 may output voice data processed through the processor 120 to the user through the speaker.

The display 150 may display various pieces of information (for example, multimedia data, text data, or the like) for the user.

The communication interface 160 connects communication between the wearable device 100 and the external device (for example, electronic device 104 or server 106). For example, the communication interface 160 may access a network 162 through a wireless or wired communication to communicate with the external device. The wireless communication may include at least one of, for example, WiFi, BlueTooth (BT), Near Field Communication (NFC), a Global Positioning System (GPS), and cellular communication (for example, LTE, LTE-A, CDMA, WCDMA, UMTS, WiBro or GSM). The wired communication may include at least one of, for example, a Universal Serial Bus (USB), a High Definition Multimedia Interface (HDMI), Recommended Standard 232 (RS-232), and a Plain Old Telephone Service (POTS).

According to an embodiment, the network 162 may be a telecommunication network. The telecommunication network includes at least one of a computer network, Internet, Internet of things, and a telephone network. According to an embodiment, a protocol (for example, transport layer protocol, data link layer protocol, or physical layer protocol) for communication between the wearable device 100 and the external device may be supported by at least one of the application 134, the application programming interface 133, the middleware 132, the kernel 131, and the communication interface 160.

According to an embodiment, the server 106 supports driving of the wearable device 100 by performing at least one operation (or function) implemented by the electronic device 101. For example, the server 106 may include a communication control server module 108 that supports the application control module 170 implemented in the electronic device 101. For example, the communication control server module 108 may include at least one of the components of the application control module 170 to perform (on behalf of) at least one operations performed by the application control module 170.

Figure 2:
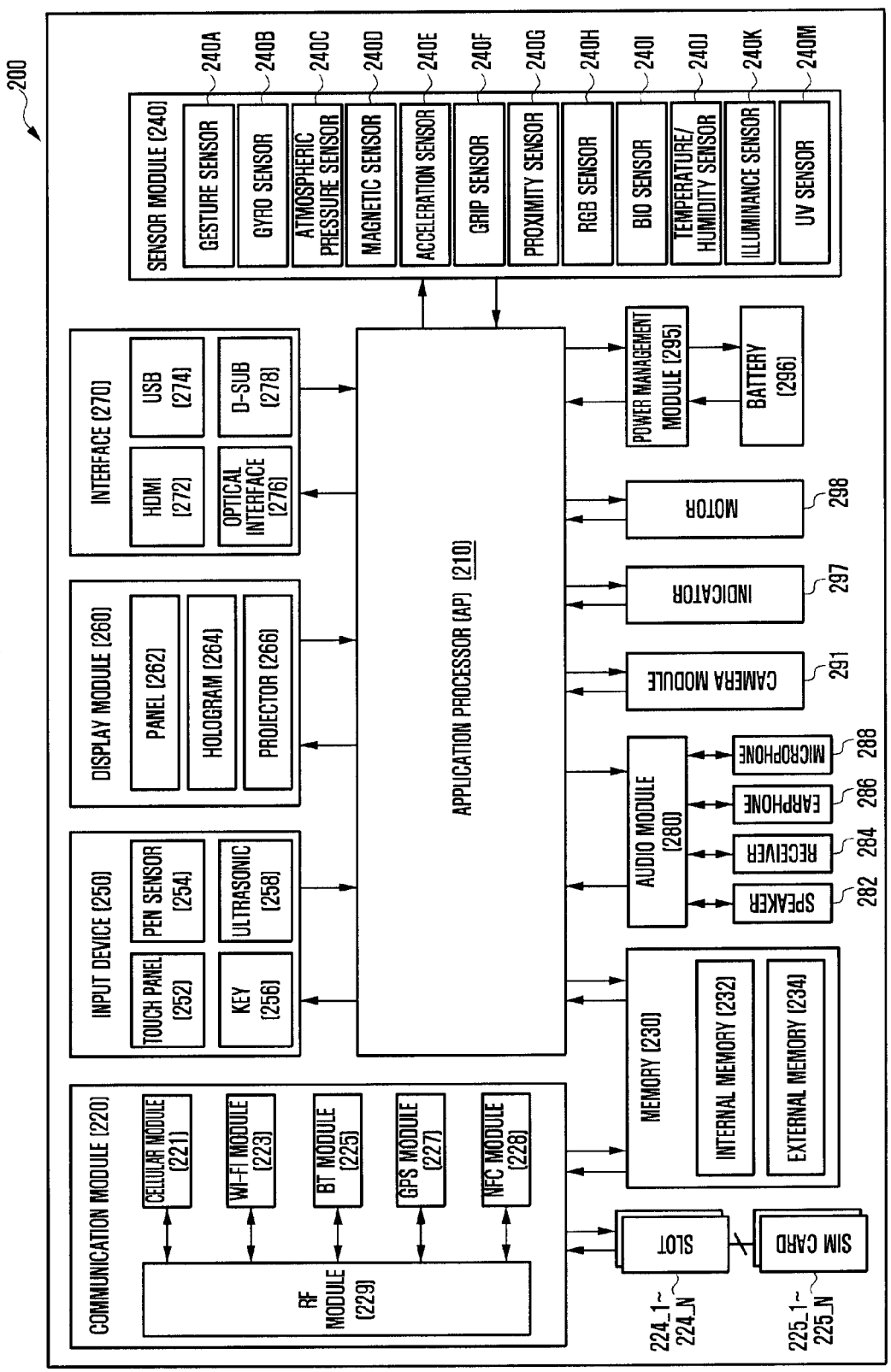
FIG. 2 is a block diagram of a wearable device according to an embodiment of the present disclosure.

FIG. 2 is a block diagram of a wearable device 200 according to an embodiment of the present disclosure. The wearable device 200 may configure, for example, a whole or a part of the wearable device 100 illustrated in FIG. 1. Referring to FIG. 2, the wearable device 200 may include one or more Application Processors (APs) 210, a communication module 220, a Subscriber Identification Module (SIM) card 224, a memory 230, a sensor module 240, an input device 250, a display 260, an interface 270, an audio module 280, a camera module 291, a power managing module 295, a battery 296, an indicator 297, and/or a motor 298.

The AP 210 operates an operating system (OS) or an application program so as to control a plurality of hardware or software component elements connected to the AP 210 and execute various data processing and calculations including multimedia data. The AP 210 may be implemented by, for example, a System on Chip (SoC). According to an embodiment, the processor 210 may further include a Graphic Processing Unit (GPU).

The communication module 220 (for example, communication interface 160) may transmit/receive data in communication between different electronic devices (for example, the electronic device 104 and the server 106) connected to the wearable device 200 (for example, electronic device 101) through a network. According to an embodiment, the communication module 220 may include a cellular module 221, a WiFi module 223, a BlueTooth (BT) module 225, a Global Positioning System (GPS) module 227, a Near Field Communication (NFC) module 228, and/or a Radio Frequency (RF) module 229.

The cellular module 221 may provide a voice, a call, a video call, a Short Message Service (SMS), or an Internet service through a communication network (for example, Long Term Evolution (LTE), LTE-A, Code Division Multiple Access (CDMA), Wideband CDMA (WCDMA), UMTS, WiBro, GSM or the like). Further, the cellular module 221 may distinguish and authenticate electronic devices within a communication network by using a subscriber identification module (for example, the SIM card 224). According to an embodiment, the cellular module 221 may perform at least some of the functions which can be provided by the AP 210. For example, the cellular module 221 may perform at least some of the multimedia control functions.

According to an embodiment, the cellular module 221 may include a Communication Processor (CP). Further, the cellular module 221 may be implemented by, for example, an SoC.

Although the components such as the cellular module 221 (for example, communication processor), the memory 230, and the power managing module 295 are illustrated as components separate from the AP 210 in FIG. 8, the AP 210 may include at least some (for example, cellular module 221) of the aforementioned components in an embodiment.

According to an embodiment, the AP 210 or the cellular module 221 (for example, communication processor) may load a command or data received from at least one of a non-volatile memory and other components connected to each of the AP 210 and the cellular module 221 to a volatile memory and process the loaded command or data. Further, the AP 210 or the cellular module 221 may store data received from at least one of other components or generated by at least one of other components in a non-volatile memory.

Each of the WiFi module 223, the BT module 225, the GPS module 227, and the NFC module 228 may include, for example, a processor for processing data transmitted/received through the corresponding module. Although the cellular module 221, the WiFi module 223, the BT module 225, the GPS module 227, and the NFC module 228 are illustrated as blocks separate from each other in FIG. 8, at least some (for example, two or more) of the cellular module 221, the WiFi module 223, the BT module 225, the GPS module 227, and the NFC module 228 may be included in one Integrated Chip (IC) or one IC package according to one embodiment. For example, at least some (for example, the communication processor corresponding to the cellular module 221 and the WiFi processor corresponding to the WiFi module 223) of the processors corresponding to the cellular module 221, the WiFi module 223, the BT module 225, the GPS module 227, and the NFC module 228 may be implemented by one SoC.

The RF module 229 may transmit/receive data such as, for example, an RF signal. Although not illustrated, the RF module 229 may include, for example, a transceiver, a Power Amp Module (PAM), a frequency filter, a Low Noise Amplifier (LNA) or the like. Further, the RF module 229 may further include a component for transmitting/receiving electronic waves over a free air space in wireless communication, for example, a conductor, a conducting wire, or the like. Although the cellular module 221, the WiFi module 223, the BT module 225, the GPS module 227, and the NFC module 228 share one RF module 229 in FIG. 2, at least one of the cellular module 221, the WiFi module 223, the BT module 225, the GPS module 227, and/or the NFC module 228 may transmit/receive a signal, e.g., an RF signal, through a separate RF module according to one embodiment.

The SIM card 224 is a card including a Subscriber Identification Module and may be inserted into a slot formed in a particular portion of the electronic device. The SIM card 224 may include unique identification information (for example, Integrated Circuit Card IDentifier (ICCID)) or subscriber information (for example, International Mobile Subscriber Identity (IMSI)).

The memory 230 (for example, memory 130) may include an internal memory 232 or an external memory 234. The internal memory 232 may include, for example, at least one of a volatile memory (for example, a Random Access Memory (RAM), a dynamic RAM (DRAM), a static RAM (SRAM), a synchronous dynamic RAM (SDRAM), and the like), and a non-volatile Memory (for example, a Read Only Memory (ROM), a one time programmable ROM (OTPROM), a programmable ROM (PROM), an erasable and programmable ROM (EPROM), an electrically erasable and programmable ROM (EEPROM), a mask ROM, a flash ROM, a NAND flash memory, an NOR flash memory, and the like).

According to an embodiment, the internal memory 232 may be a Solid State Drive (SSD). The external memory 234 may further include a flash drive, for example, a Compact Flash (CF), a Secure Digital (SD), a Micro Secure Digital (Micro-SD), a Mini Secure Digital (Mini-SD), an extreme Digital (xD), or a memory stick. The external memory 234 may be functionally connected to the wearable device 200 through various interfaces. According to an embodiment, the wearable device 200 may further include a storage device (or storage medium) such as a hard drive.

The sensor module 240 may measure a physical quantity or detect an operation state of the electronic device 201, and may convert the measured or detected information into an electronic signal. The sensor module 240 may include, for example, at least one of a gesture sensor 240A, a gyro sensor 240B, an atmospheric pressure (barometric) sensor 240C, a magnetic sensor 240D, an acceleration sensor 240E, a grip sensor 240F, a proximity sensor 240G, a color sensor 240H (for example, Red, Green, and Blue (RGB) sensor) 240H, a biometric sensor 240I, a temperature/humidity sensor 240J, an illumination (light) sensor 240K, and/or an Ultra Violet (UV) sensor 240M. Additionally or alternatively, the sensor module 240 may include, for example, a E-nose sensor, an electromyography (EMG) sensor, an electroencephalogram (EEG) sensor, an electrocardiogram (ECG) sensor, an Infra-Red (IR) sensor, an iris sensor, a fingerprint sensor (not illustrated), and the like. The sensor module 240 may further include a control circuit for controlling one or more sensors included in the sensor module 240.

The input device 250 may include a touch panel 252, a (digital) pen sensor 254, a key 256, and/or an ultrasonic input device 258. For example, the touch panel 252 may recognize a touch input in at least one type of a capacitive type, a resistive type, an infrared type, and an acoustic wave type. The touch panel 252 may further include a control circuit. Where the touch input is of the capacitive type, the touch panel 252 may recognize proximity as well as a direct touch. The touch panel 252 may further include a tactile layer such that the touch panel 252 may provide a tactile reaction to the user.

The (digital) pen sensor 254 may be implemented, for example, using a method identical or similar to a method of receiving a touch input of the user, or using a separate recognition sheet. The key 256 may include, for example, a physical button, an optical key, or a key pad. The ultrasonic input device 258 is a device that can detect an acoustic wave by a microphone (for example, microphone 288) of the wearable device 200 through an input means generating an ultrasonic signal to identify data and can perform wireless recognition. According to an embodiment, the wearable device 200 may receive a user input from an external device (for example, computer or server) connected to the wearable device 200 by using the communication module 220.

The display 260 (for example, display 150) may include a panel 262, a hologram device 264, and a projector 266. The panel 262 may be, for example, a Liquid Crystal Display (LCD) or an Active Matrix Organic Light Emitting Diode (AM-OLED). The panel 262 may be implemented to be, for example, flexible, transparent, or wearable. The panel 262 may be configured or controlled via the touch panel 252. The hologram device 264 shows a stereoscopic image in the air by using interference of light. The projector 266 may project light on a screen to display an image. For example, the screen may be located inside or outside the electronic device 201. According to an embodiment, the display 260 may further include a control circuit for controlling the panel 262, the hologram device 264, and/or the projector 266.

The interface 270 may include, for example, a High-Definition Multimedia Interface (HDMI) 272, a Universal Serial Bus (USB) 274, an optical interface 276, and a D-subminiature (D-sub) 278. The interface 270 may be included in, for example, the communication interface 160 illustrated in FIG. 1. Additionally or alternatively, the interface 290 may include, for example, a Mobile High-definition Link (MHL) interface, a Secure Digital (SD) card/Multi-Media Card (MMC), and/or an Infrared Data Association (IrDA) standard interface.

The audio module 280 may bi-directionally convert a sound and an electronic signal. At least some components of the audio module 280 may be included in, for example, the input/output interface 140 illustrated in FIG. 1. The audio module 280 processes sound information input or output through, for example, a speaker 282, a receiver 284, an earphone 286, the microphone 288 or the like.

The camera module 291 is a device which can photograph a still image and a video. According to an embodiment, the camera module 291 may include one or more image sensors (for example, a front sensor or a back sensor), an Image Signal Processor (ISP) (not shown) or a flash (for example, an LED or xenon lamp).

The power managing module 295 manages power of the electronic device 201. Although not illustrated, the power managing module 295 may include, for example, a Power Management Integrated Circuit (PMIC), a charger Integrated Circuit (IC), and/or a battery or fuel gauge.

The PMIC may be mounted to, for example, an integrated circuit or an SoC semiconductor. A charging method may be divided into wired and wireless methods. The charger IC charges a battery and prevent over voltage or over current from flowing from a charger. According to an embodiment, the charger IC includes a charger IC for at least one of the wired charging method and the wireless charging method. The wireless charging method may include, for example, a magnetic resonance method, a magnetic induction method and an electromagnetic wave method, and additional circuits for wireless charging, for example, circuits such as a coil loop, a resonant circuit, a rectifier or the like may be added.

The battery fuel gauge measures, for example, a remaining quantity of the battery 296, or a voltage, a current, or a temperature during charging. The battery 296 may store or generate electricity and supply power to the wearable device 200 by using the stored or generated electricity. The battery 296 may include a rechargeable battery or a solar battery.

The indicator 297 shows particular statuses of the wearable device 200 or a part (for example, AP 210) of the electronic device 201, for example, a booting status, a message status, a charging status and the like. The motor 298 converts an electrical signal to a mechanical vibration.

Although not illustrated, the wearable device 200 may include a processing unit (for example, GPU) for supporting a module TV. The processing unit for supporting the mobile TV may process, for example, media data according to a standard of Digital Multimedia Broadcasting (DMB), Digital Video Broadcasting (DVB), media flow or the like.

Each of the components of the electronic device according to various embodiments of the present disclosure may be implemented by one or more components and the name of the corresponding component may vary depending on a type of the electronic device. The electronic device according to various embodiments of the present disclosure may include at least one of the above described components, a few of the components may be omitted, or additional components may be further included. Also, some of the components of the electronic device according to various embodiments of the present disclosure may be combined to form a single entity, and thus may equivalently execute functions of the corresponding components before being combined.

The term "module" used in the present disclosure may refer to, for example, a unit including one or more combinations of hardware, software, and firmware. The "module" may be interchangeable with a term, such as "unit," "logic," "logical block," "component," "circuit," or the like. The "module" may be a minimum unit of a component formed as one body or a part thereof. The "module" may be a minimum unit for performing one or more functions or a part thereof. The "module" may be implemented mechanically or electronically. For example, the "module" according to an embodiment of the present disclosure may include at least one of an Application-Specific Integrated Circuit (ASIC) chip, a Field-Programmable Gate Array (FPGA), and a programmable-logic device for performing certain operations, which have been known or are to be developed in the future.

Figure 3:
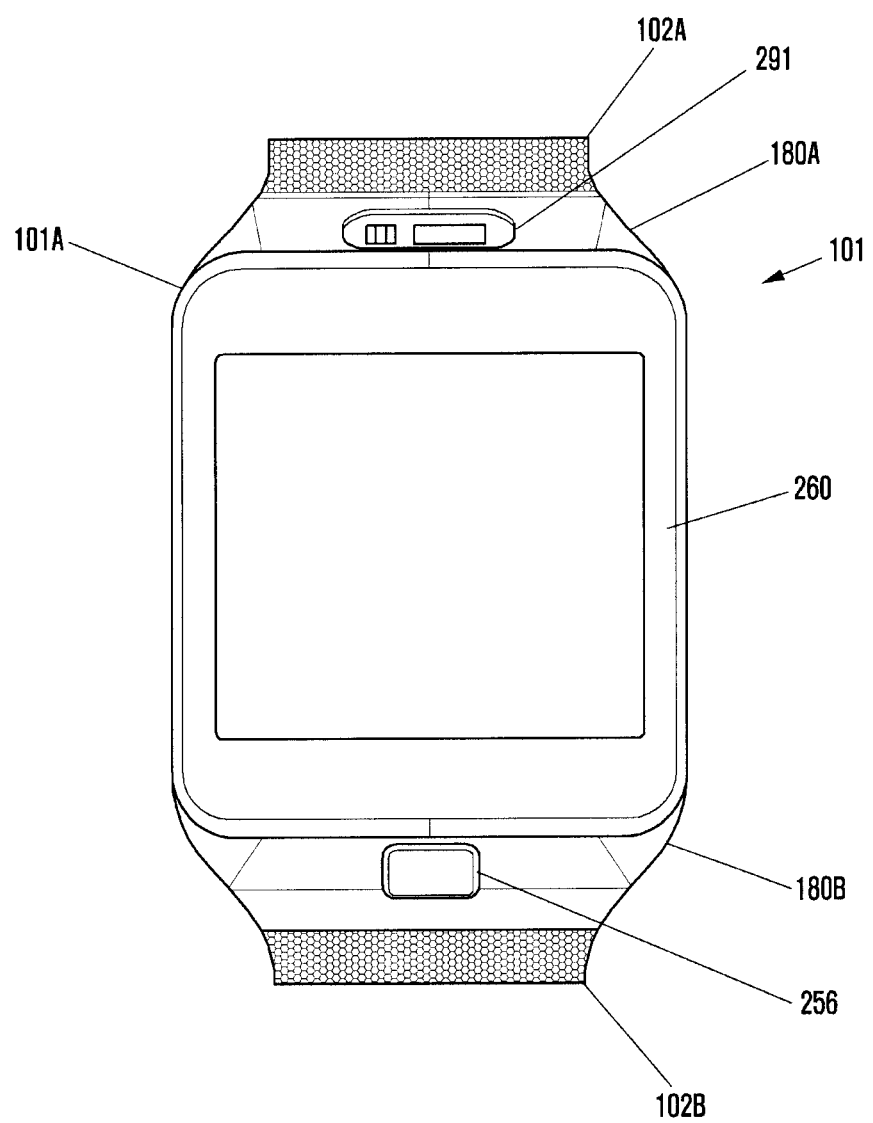
FIG. 3 is a front view of a wearable device according to an embodiment of the present disclosure.

FIG. 3 is a front view of a wearable device according to embodiments of the present disclosure.

The wearable device 200 may include a display 260, a camera module 291, a key 256, a body 101 and/or a band 102. The band 102 may include an upper band 102A, connected to an upper side 180A of the body 101, and/or a lower band 102B connected to a lower side 180B of the body 101.

The body 101 may include the display 260, the camera module 291 and/or the key 256 on the front. The body 101 is formed a housing 101A. The housing 101A may be connected to a cover 101B placed at the lower portion. The housing 101A and the cover 101B may form an internal space where electric parts are placed. The body 101 may include: a front, which may be shaped as a rounded square or a rounded rectangle, and a back opposite to the front. An upper side 180A and a lower side 180B may couple the front and back and may be between the front and the back. The left side and the right side may couple the front and back and may be between the front and the back. The body 101 may form the sides by the upper sides 180A, the lower sides 180B, the left side, and the right side, which are between the front and the back. The upper side 180A may form an obtuse angle with the front of the body 101 and an acute angle with the back of the body 101. The lower side 180B may form an obtuse angle with the front of the body 101 and an acute angle with the back of the body 101. The upper side 180A may form a groove. The camera module 291 may include a lens (or a camera window 2913), and may be located within the groove and exposed to the outside, in the groove. The key 256 may be placed at the lower side 180B of the body 101 and may extend or protrude therefrom. The left side and the right side may be positioned opposite one another with respect to the display 260. The upper side 180A and the lower sides 180B may be opposite to each other with respect to the display 260.

The upper side 180A may be connected to the upper band 102A. The lower side 180B may be connected to the lower band 102B. The body 101 may form slope portions (180A, 180B) part of which may be sloped in the direction to be worn on the human body (e.g., wrist) respectively. The slope portions (180A, 180B) may include a first slope potion 180A and a second slope portion 180B formed at both sides of the body 101. In the disclosure, the first slope portion 180A may be referred to as the upper side 180A and the second slope portion 180B may be referred to as the lower side 180B. When viewing the front of the wearable device 200, the body 101 may be formed in such a way that each of the both sides may be wider closer to the display 260 and narrower closer to the band 102A or 102B. For example, when viewing the front of the wearable device 200, each of the both sides of the body 101 may be shaped as a curved isosceles trapezoid so that it is wider closer to the display 260 and narrower closer to the band 102A or 102B. It may be modified in such a way that, when viewing the front of the wearable device 200, the both sides of the body 101 may be shaped as asymmetric forms as an aesthetic design element.

The camera module 291 may be located adjacent to the display 260. The camera module 291 may be located at the upper side 180A adjacent to the display 260. The camera module 291 may be located at the upper side 180A between the display 260 and the upper band 102A.

The upper side 180A may be sloped along the side of the wearable device 200 in such a way that one end of the upper side 180A connected to the display 260 is higher than the other end connected to the upper band 102A.

The key 256 may be located adjacent to the display 260. The key 256 may be located at the lower side 180B adjacent to the display 260. The key 256 may be located at the lower side 180B between the display 260 and the lower band 102B. The lower side 180B may sloped along the side of the wearable device 200 in such a way that one end of the lower side 180B connected to the display 260 is higher than the other end connected to the lower band 102B. For example, the wearable device 200 may include a mechanical button (e.g., direction keys, volume key), an optical key, a key pad, or the like, as well as the key 256. The mechanical button (e.g., direction keys, volume key), optical key, key pad, or the like, may be located adjacent to the display 260. The mechanical button (e.g., direction keys, volume key), optical key, key pad, or the like, may be located at the lower portion of the body 101 adjacent to the display 260. The mechanical button (e.g., direction keys, volume key), optical key, key pad, or the like, may be located at the lower portion of the body 101 between the display 260 and the lower band 102B.

The body 101 may be made of a synthetic material, plastics (e.g., ABS, polycarbonate), ceramic, wood, metal (e.g., polished aluminum), metal alloy (e.g., steel, stainless steel), titanium- or magnesium-based alloy, or the like.

The body 101 may be formed in such a way that the both ends are connected to the band 102 that are worn on the human body (e.g., wrist or arm).

The body 101 may store an application processor 210 (or processor 120) for controlling the wearable device 200, a communication module 220 for communicating with a base station, a server or an external communication device via a communication network, a sensor module 240 for measuring physical quantities, detecting operation states of the wearable device 200, and converting measured or detected information to electrical signals, a touch panel 252 for sensing a user's touch inputs (including direct touches or proximity touches), a speaker for outputting voices, a camera module 291 for taking still images or moving images, a battery, etc.

The band 102 may be made of metal, textile, leather, rubber, synthetic fiber, wood, ceramic, plastics, or the like. The band 102 may be layered with various materials. The band 102 may include a conductive material that can be electrically connected to the electronic parts stored in the body 101. The band 102 may be a wearable tool that is attached to part of the housing 101A and worn on part of an external object (e.g., the human body).

Figure 4:
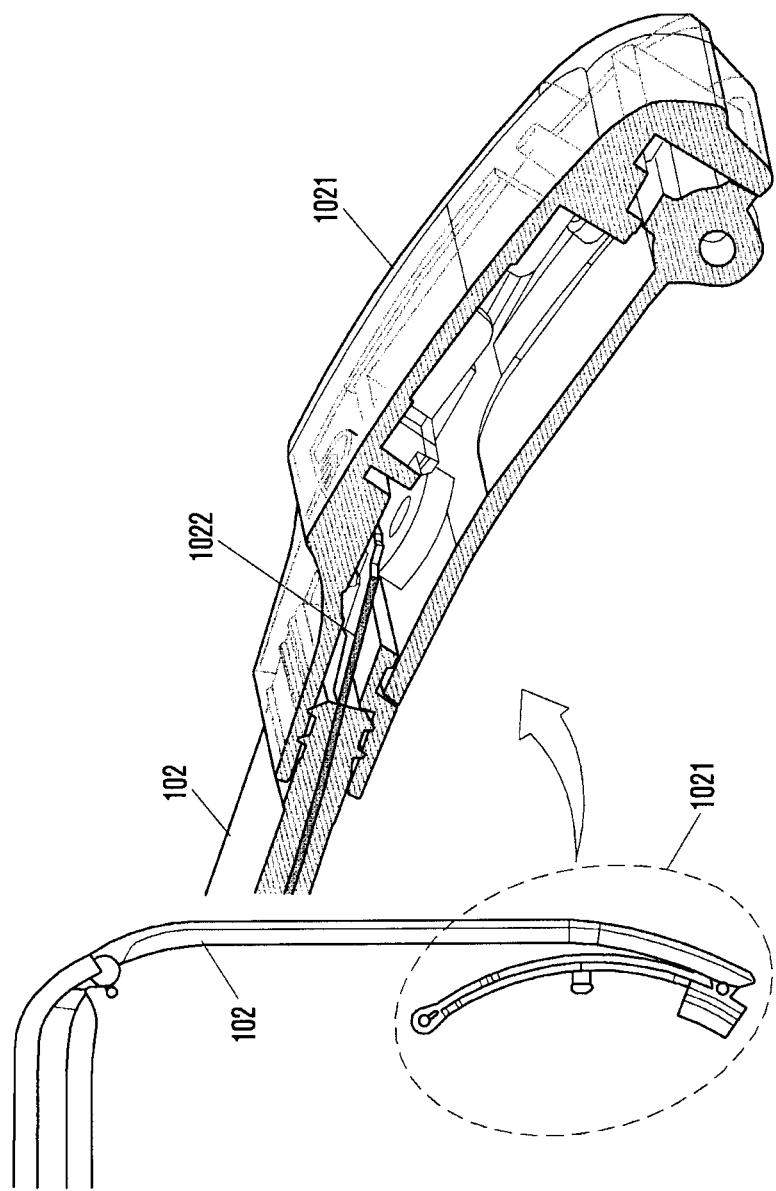
FIG. 4 is a cross-sectional perspective view of a fastener according to an embodiment of the present disclosure.

FIG. 4 is a cross-sectional perspective view of a fastener 1021 according to embodiments of the present disclosure.

Referring to FIGS. 3 and 4, the band 102 may be conductive in such a way that it is covered with a conductive material 1022. The band 102 may include covered electric wires in its body. The band 102 may include electric wires that are layered with at least one wire being layered upon another wire. The conductive material 1022 may electrically connect parts in the body 101 to parts in a fastener 1021.

The band 102 may include a fastener 1021 that allows users to detachably attach the wearable device 200 to his/her body (e.g., wrist, arm, etc.). Examples of the fastener 1021 may be a buckle, a snap-fitting hook, a fabric hook and loop fastener, etc. The fastener 1021 may store a module (e.g., a camera module, a projector, etc.). The fastener 1021 may be formed in such a way that its part is elastic.

Figure 5:
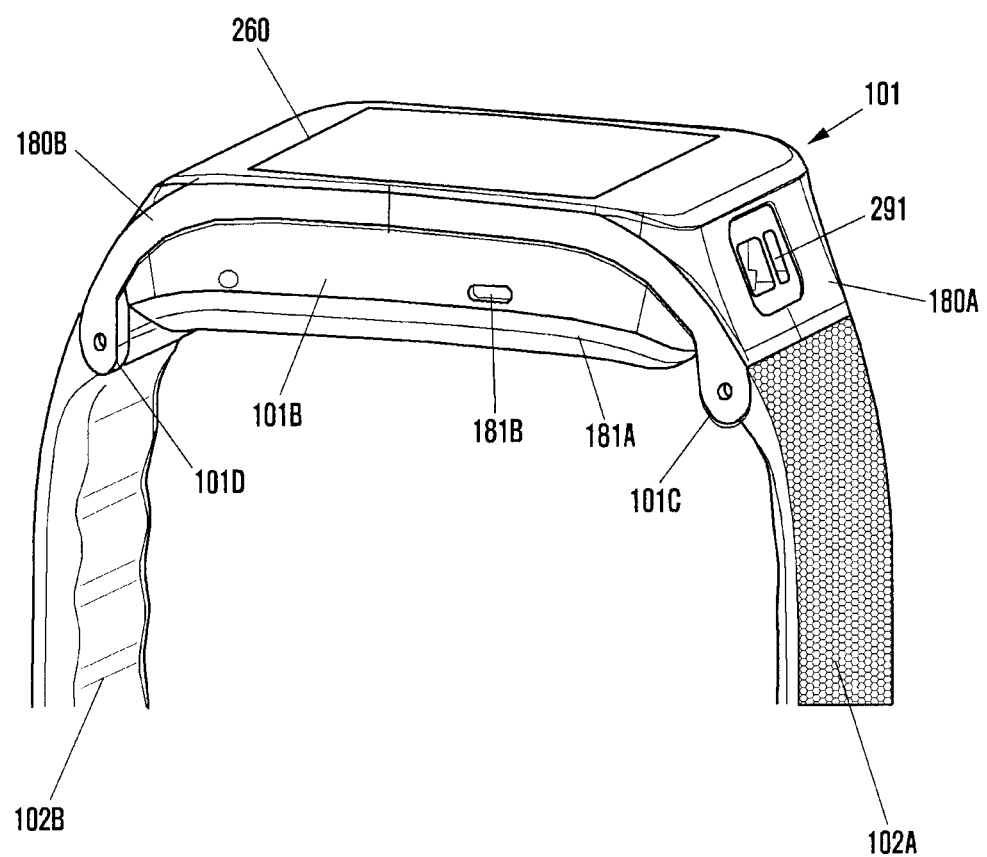
FIG. 5 is a right side view of a wearable device according to an embodiment of the present disclosure.

FIG. 5 is a right side view of a wearable device according to embodiments of the present disclosure.

When viewing the side of the wearable device 200, the body 101 and the display 260 may be curved along to correspond to the shape of the human body (e.g., wrist). The body 101 may form slope portions (180A, 180B) part of which are sloped in the direction to be worn on the human body (e.g., wrist) respectively. The body 101 forms holes 101C and 101D at the both ends, into which pins may be inserted to connect the band 102A and 101B to the both ends. The bands 102A and 102B may attach dielectric supports to end(s) of the bands so that they can secure strength and firmly hold the pins in the holes 101C and 101D, respectively. When viewing the side of the wearable device 200, the upper hole 101C may be located under the camera module 291 and connected to the upper band 102A. The lower hole 101D may be located under the key 256 and connected to the lower band 102B. With the holes 101C and 101D formed at both ends of the body 101, the bands 102A and 102B are positioned such that an angle of view of the camera module 291 is not blocked. At least one of the holes 101C and 101D may be formed at the ends of four corners of the body 101. The terms band coupling unit 101C and 101D as used herein refers to the bands 102A and 102B where they include at least one of the holes 101C and 101D.

The wearable device 200 may be configured such that the body 101 forms locking grooves 181A and 181B at the left and right side, so that it can be connected to an external electronic device (e.g., a charger). The wearable device 200 may include a left locking groove 181A and a right locking groove 181B sot that it can be connected to an external electronic device (e.g., a charger). In another embodiment of the present disclosure, the wearable device 200 may further include a detachable charger.

Figure 6A:
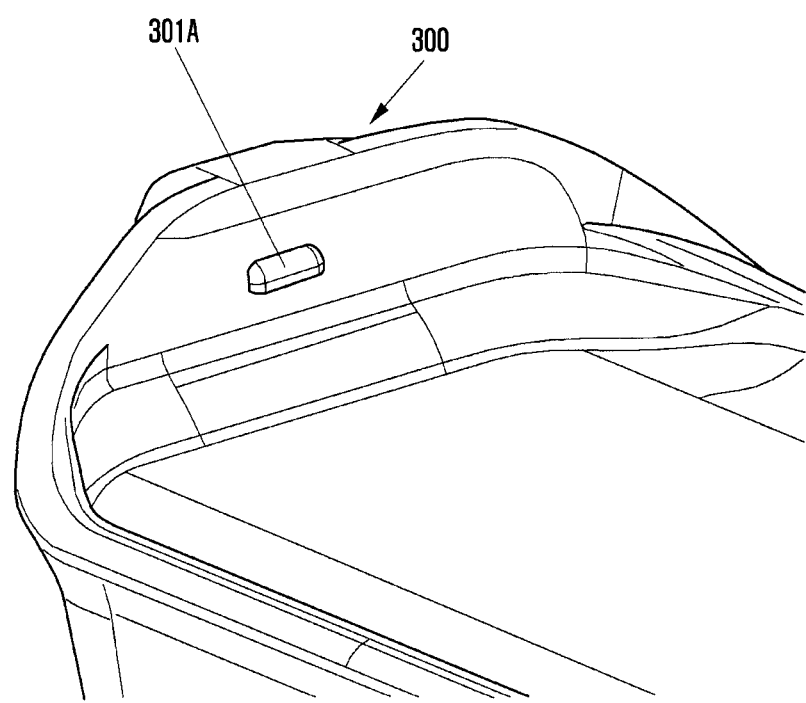
FIG. 6A is a view of part of an external electronic device according to an embodiment of the present disclosure.
Figure 6B:
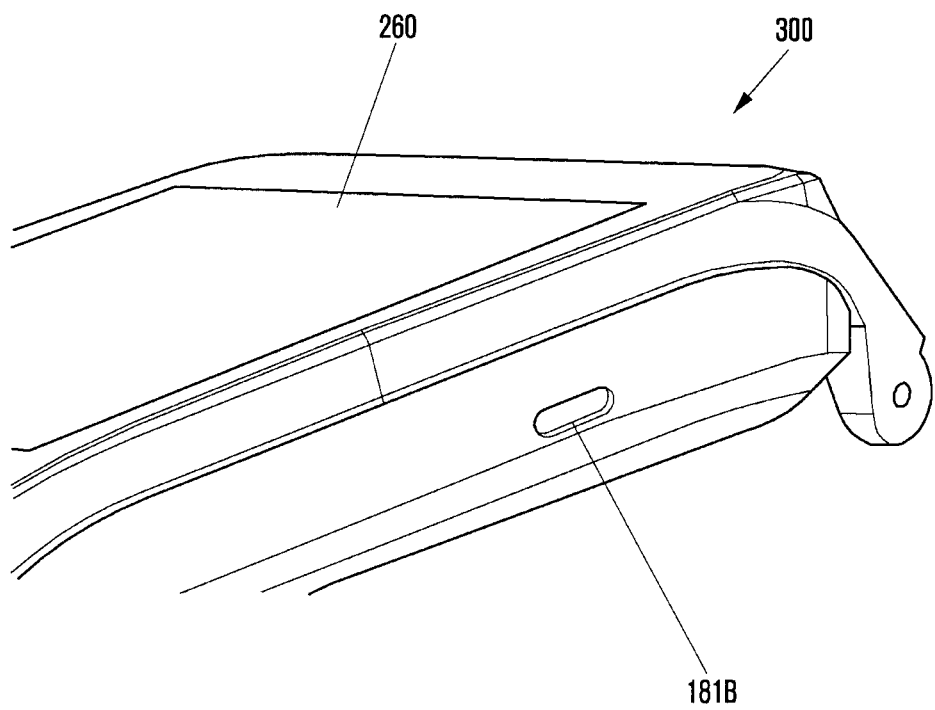
FIG. 6B is a view of part of a wearable device with locking grooves according to an embodiment of the present disclosure.
Figure 6C:
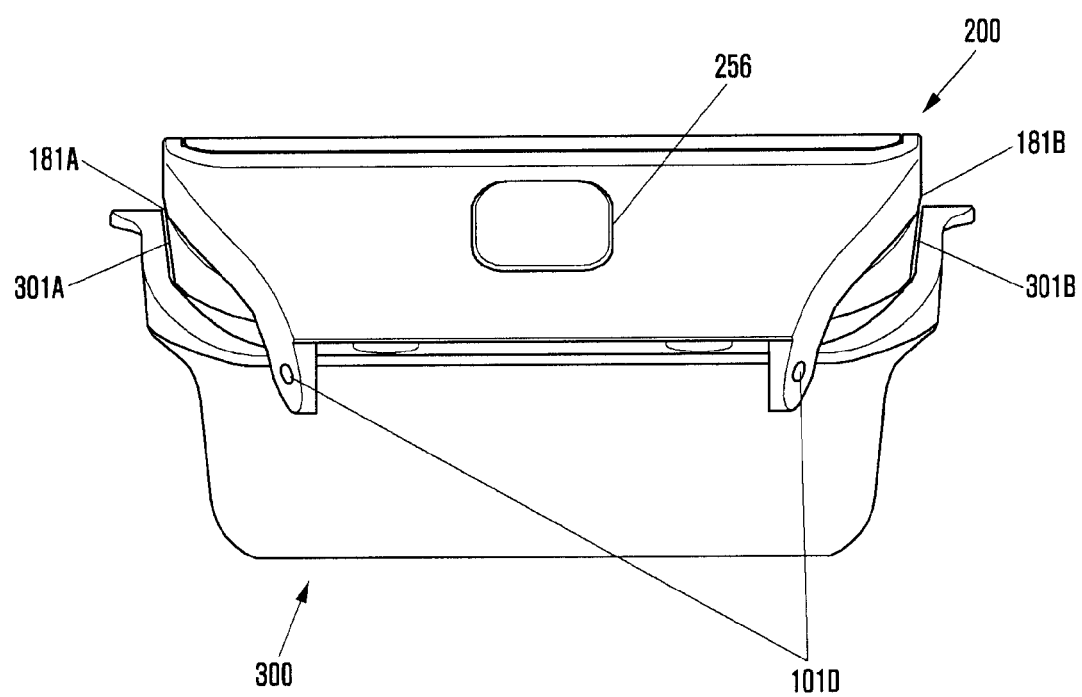
FIG. 6C is a view showing a state where a wearable device and an external electronic device are coupled to each other.

FIG. 6A is a view of part of an external electronic device 300 according to embodiments of the present disclosure. FIG. 6B is a view of part of a wearable device with locking grooves 181A and 181B according to embodiments of the present disclosure. FIG. 6C is a view showing a state where a wearable device 200 and an external electronic device 300 are coupled to each other.

Referring to FIGS. 6A to 6C, the external electronic device 300 may include wing-shaped hooks 301A and 301B to which the wearable device 200 is detachably attached. The external electronic device 300 forms a concave surface. When the wearable device 200 may be coupled to the external electronic device 300, part of the left side, right side and back of the wearable device 200 may contact the concave surface of the external electronic device 300. The external electronic device 300 may include a support (or cradle) for coupling to the wearable device 200. The left locking groove 181A of the wearable device 200 may be coupled to the left hook 301A of the external electronic device 300. The right locking groove 181B of the wearable device 200 may be coupled to the right hook 301B of the external electronic device 300. The external electronic device 300 may be designed in such a way as to surround part of the sides and the back of the wearable device 200. The external electronic device 300 may be facing part of the back, the left and the right side of the wearable device 200.

Figure 7A:
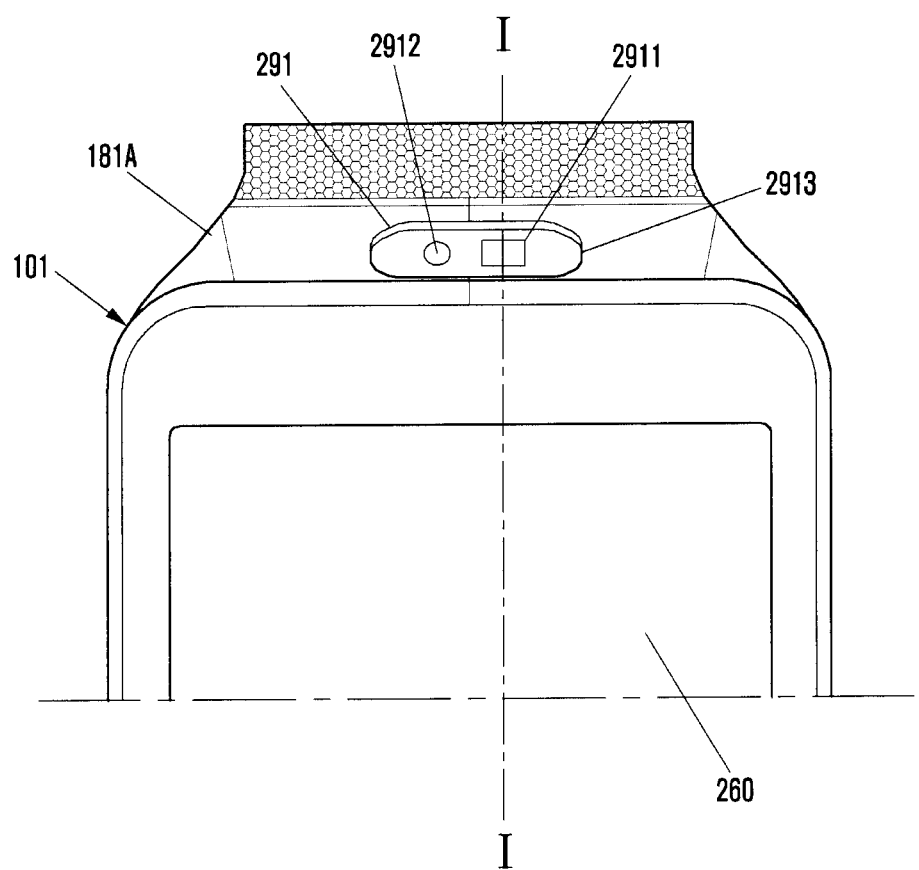
FIG. 7A is a view of a camera module according to embodiments of the present disclosure.
Figure 7B:
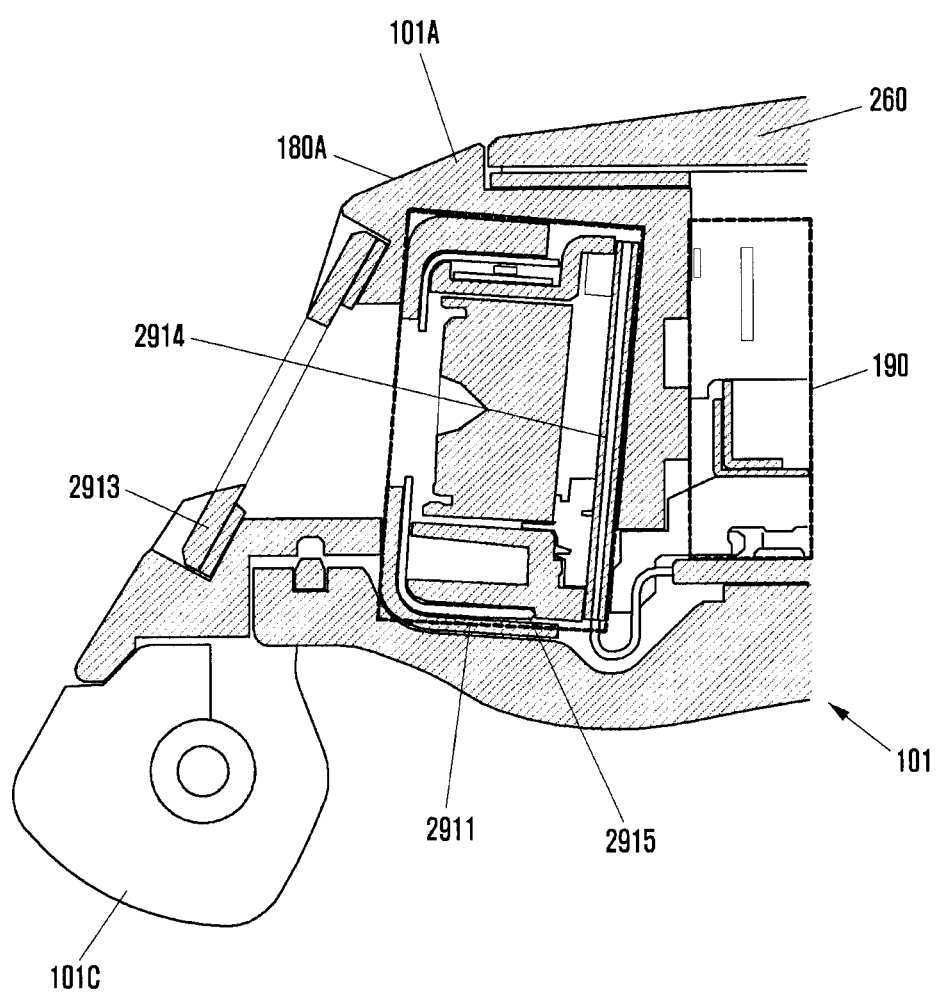
FIG. 7B is a cross-sectional view of the camera module of FIG. 7A, taken along line I-I of FIG. 7A.

FIG. 7A is a view of a camera module 291 according to embodiments of the present disclosure. FIG. 7B is a cross-sectional view of the camera module 291, taken along line I-I of FIG. 7A.

Referring to FIGS. 7A and 7B, the body 101 may have at least a part that may be sloped to the direction to be worn on the human body (e.g., wrist) at the same slope angle as the upper side 180A. The wearable device 200 may include a first slope portion 180A formed at the upper ends of the body 101, respectively. When viewing the front of the wearable device 200, the upper side 180A may be formed in such a way that it is wide closer to the display 260 and narrow closer to the upper band 102A. For example, when viewing the front of the wearable device 200, the upper side 180A is shaped as a curved isosceles trapezoid so that it is wide closer to the display 260 and narrow closer to the upper band 102A. It may be modified in such a way that, when viewing the front of the wearable device 200, the upper side 180A of the body 101 may be shaped as an asymmetric form as an aesthetic design element.

The camera module 291 may be located adjacent to the display 260. The camera module 291 may be located at the upper side 180A of the body 101 adjacent to the display 260. The camera module 291 may be located at the upper side 180A of the body 101 between the display 260 and the upper band 102A.

The camera module 291 may include an image sensor unit 2911 and a camera window 2913. The camera window 2913 may be sloped at the same slope as the upper side 180A. The camera window 2913 may be designed to cover the image sensor unit 2911. The camera window 2913 may be made of plastic or toughened glass. The camera window 2913 may have a transparent area corresponding to an angle of view of the image sensor unit 2911 so that the image sensor unit 2911 can take pictures. The camera module 291 may include the image sensor unit 2911 and a lens 2915. The image sensor unit 2911 may include one or more image sensors 2914. The camera module 291 may be arranged so that the image sensors 2914 and the lens 2915 are facing the outside.

The camera module 291 may further include an infra-red transceiver 2912. The camera window 2913 may be designed to cover the image sensor unit 2911, infra-red transceiver 2912, and lens 2915 so that it can protect at least one of: the image sensor unit 2911, infra-red transceiver 2912, and lens 2915. The wearable device 200 may control external devices by infra-red signals of the infra-red transceiver 2912. The infra-red transceiver 2912 may include an infrared transmitting unit (e.g., infra-red LED) for generating infra-red signals and an infrared receiving unit (e.g., infra-red detector) for receiving infra-red signals. The wearable device 200 may execute a function or an application by a received infra-red signal.

The camera window 2913 may form a pattern by deposition or silk-screen printing, so that a window for the image sensor unit 2911 can be created at a location where the image sensor unit 2911 is placed.

The camera window 2913 may form a window for the infra-red transceiver 2912, with a pattern in dark color group (e.g., black) by deposition or silk-screen printing, at a location where the infra-red transceiver 2912 is placed, so that the infra-red transceiver 2912 cannot be seen from the outside.

The camera window 2913 may form a pattern by printing between the windows for the image sensor unit 2911 and the infra-red transceiver 2912 so that the image sensor unit 2911 and the infra-red transceiver 2912 can be discerned and the windows for the image sensor unit 2911 and the infra-red transceiver 2912 can also be discerned.

Figure 8A:
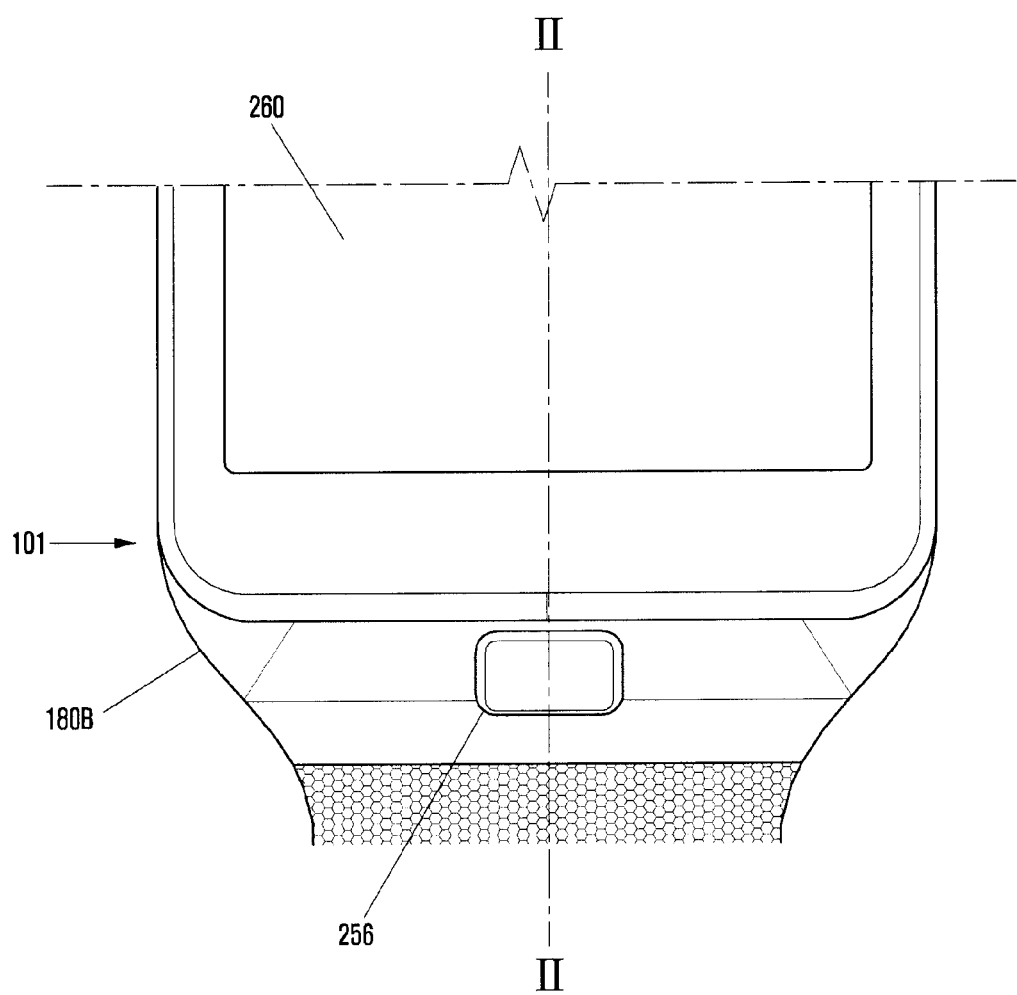
FIG. 8A is a view of a key according to embodiments of the present disclosure.
Figure 8B:
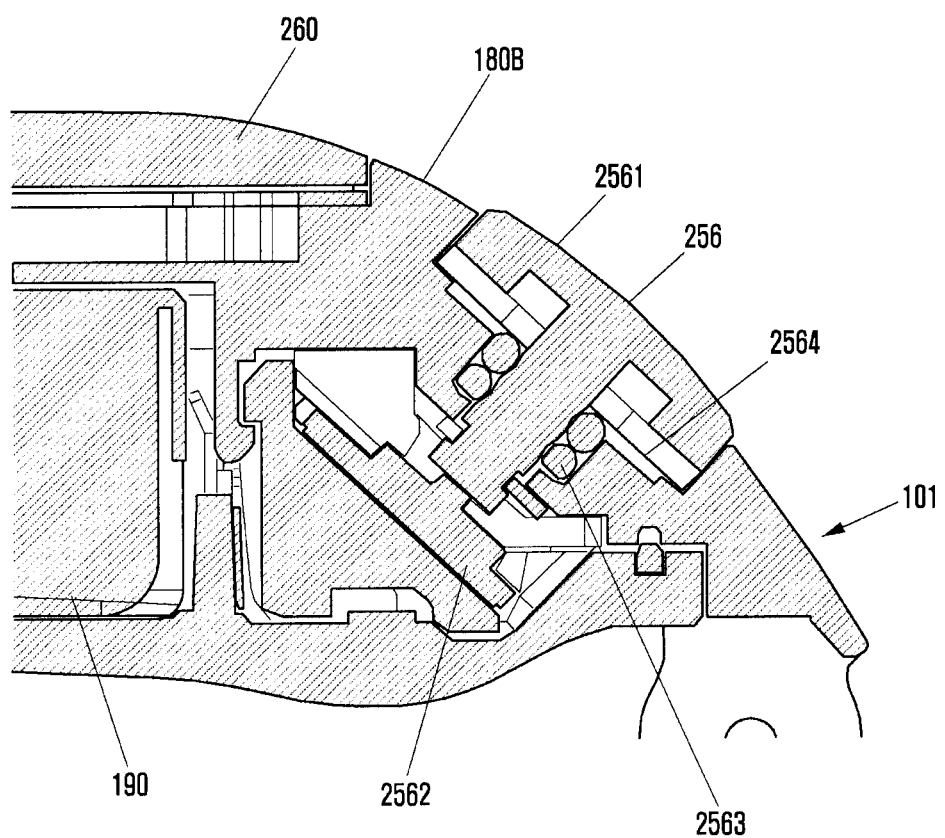
FIG. 8B is a cross-sectional view of the key, taken along line II-II of FIG. 8A.

FIG. 8A is a view of a key 256 according to embodiments of the present disclosure. FIG. 8B is a cross-sectional view of the key 256, taken along line II-II of FIG. 8A.

The body 101 may be formed to include at least a part that is sloped along the direction to be worn on the human body (e.g., wrist) at the same slope angle as the lower side 180B. The wearable device 200 may include a second slope portion 180B formed at the lower ends of the body 101, respectively. When viewing the front of the wearable device 200, the lower side 180B may be formed in such a way that it is wider closer to the display 260 and narrower closer to the lower band 102B. For example, when viewing the front of the wearable device 200, the lower side 180B may be shaped as a curved isosceles trapezoid so that it is wide closer to the display 260 and narrow closer to the lower band 102B. It may be modified in such a way that, when viewing the front of the wearable device 200, the lower side 180B of the body 101 may be shaped as an asymmetric form as an aesthetic design element.

The key 256 may be located adjacent to the display 260. The key 256 may be located at the lower side 180B of the body 101 adjacent to the display 260. The key 256 may be located at the lower side 180B of the body 101 between the display 260 and the lower band 102B.

The key 256 may receive a user's input signal by pressing. As an example of a user's input signal from the key 256, when the wearable device 200 receives a power supply control signal, it may be turned on/off. As another example of a user's input signal from the key 256, when the wearable device 200 receives a reset signal, it may be reset. As still another example of a user's input signal from the key 256, when the wearable device 200 receives a display control signal such as a signal for displaying a home screen, it may perform a corresponding display control operation such as to display a home screen.

As shown in FIG. 8B, the key 256 may include a mechanical/physical button 2561, an elastic member 2563, a water-proof ring 2564 and/or a key receiving circuit unit 2562, which may be perpendicular to the second slope portion 180B. When the mechanical/physical button 2561 is pressed by a user's inputting action, the key receiving circuit 2562 (e.g., FPCB), under the button 2561, may detect the user's pressing action. The elastic member 2563 (e.g., spring) is located between the mechanical/physical button 2561 and the key receiving circuit unit 2562. The elastic member 2563 holds the mechanical/physical button 2561 to be placed at the second slope portion 180B. The water-proof ring 2564 may be located between the mechanical/physical button 2561 and the elastic member 2563. The water-proof ring 2564 prevents water from leaking through the key 256.

Figure 9A:
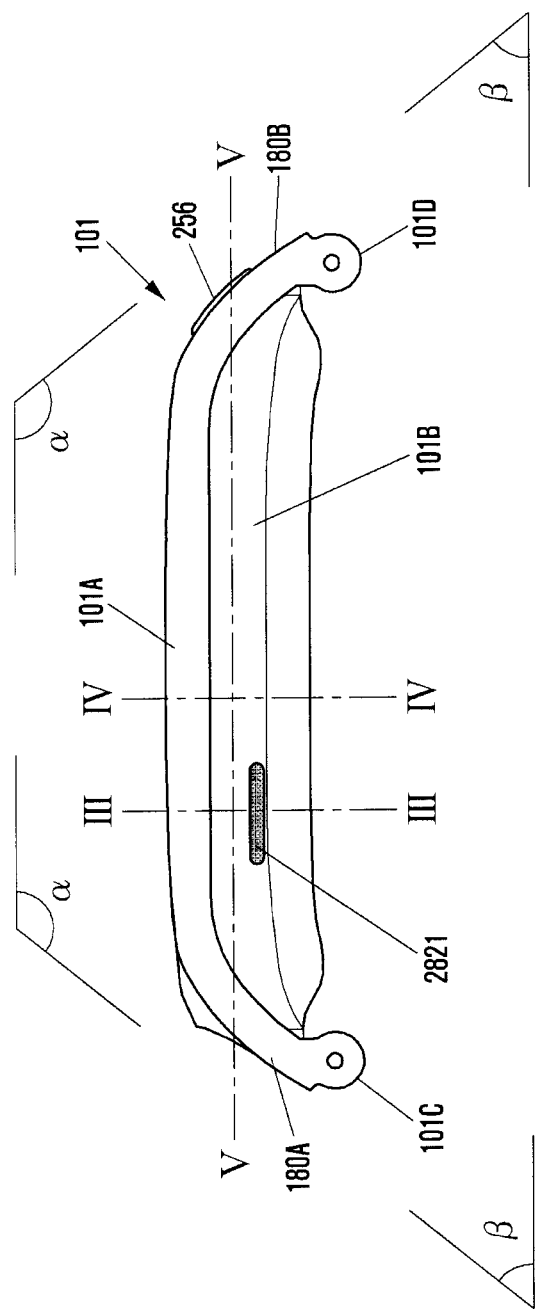
FIG. 9A is a left side view of a wearable device according to embodiments of the present disclosure.
Figure 9B:
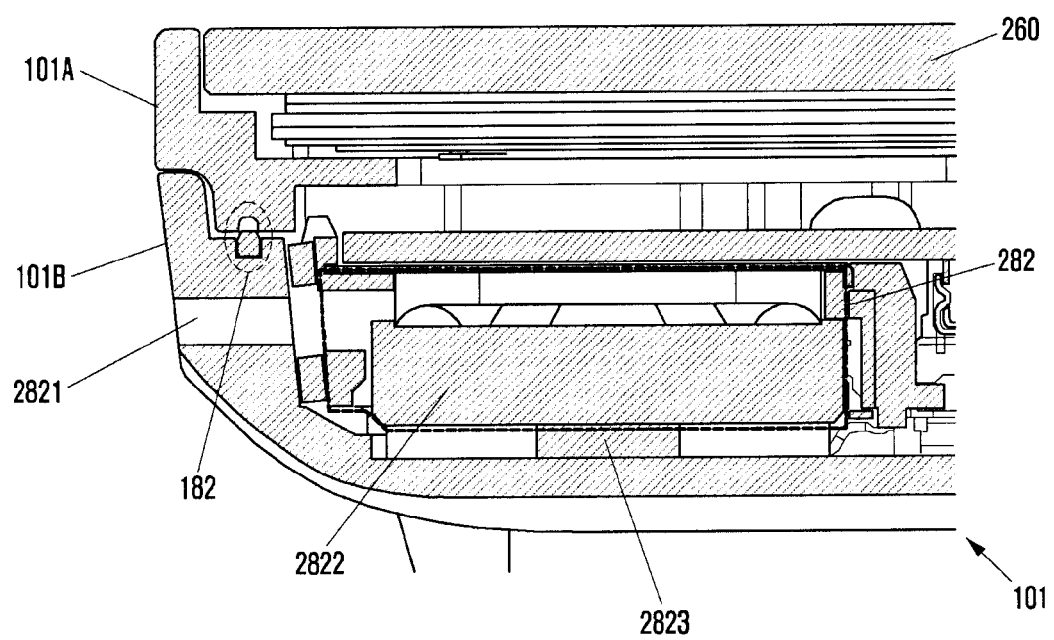
FIG. 9B is a cross-sectional view of the wearable device of FIG. 9A, taken along line III-III of FIG. 9A.
Figure 9C:
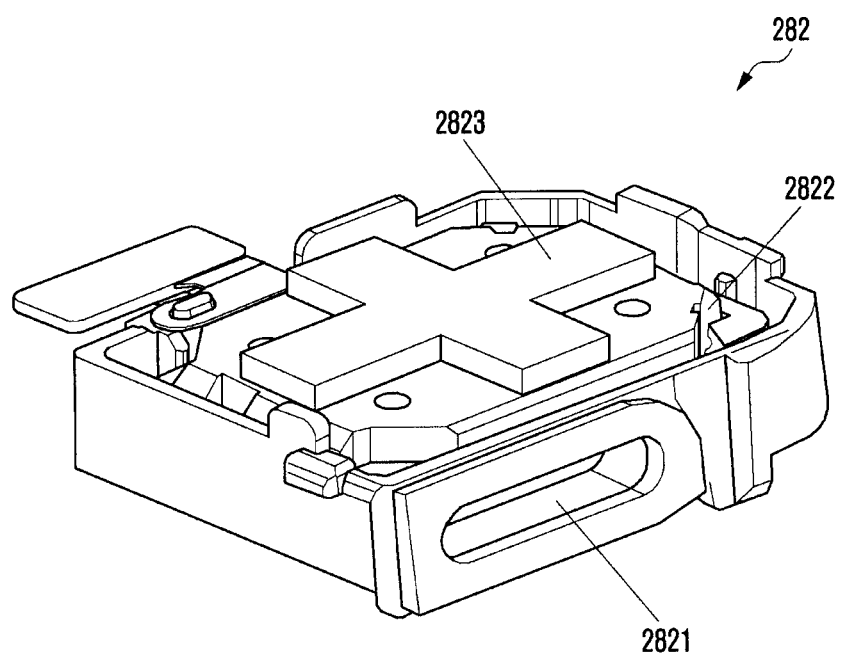
FIG. 9C is a view of a portion of the wearable device of FIG. 9A including a speaker according to an embodiment of the present disclosure.
Figure 9D:
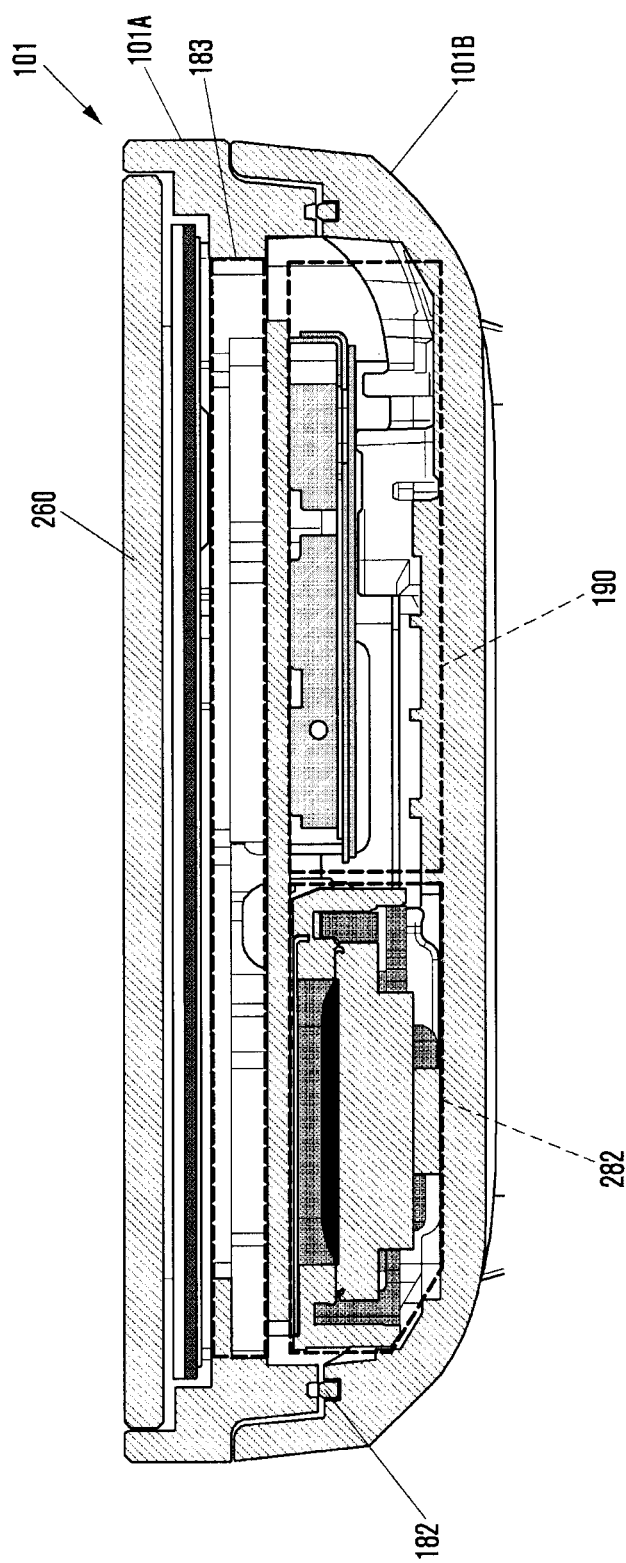
FIG. 9D is a cross-sectional view of the wearable device of FIG. 9A, taken along line IV-IV of FIG. 9A.
Figure 9E:
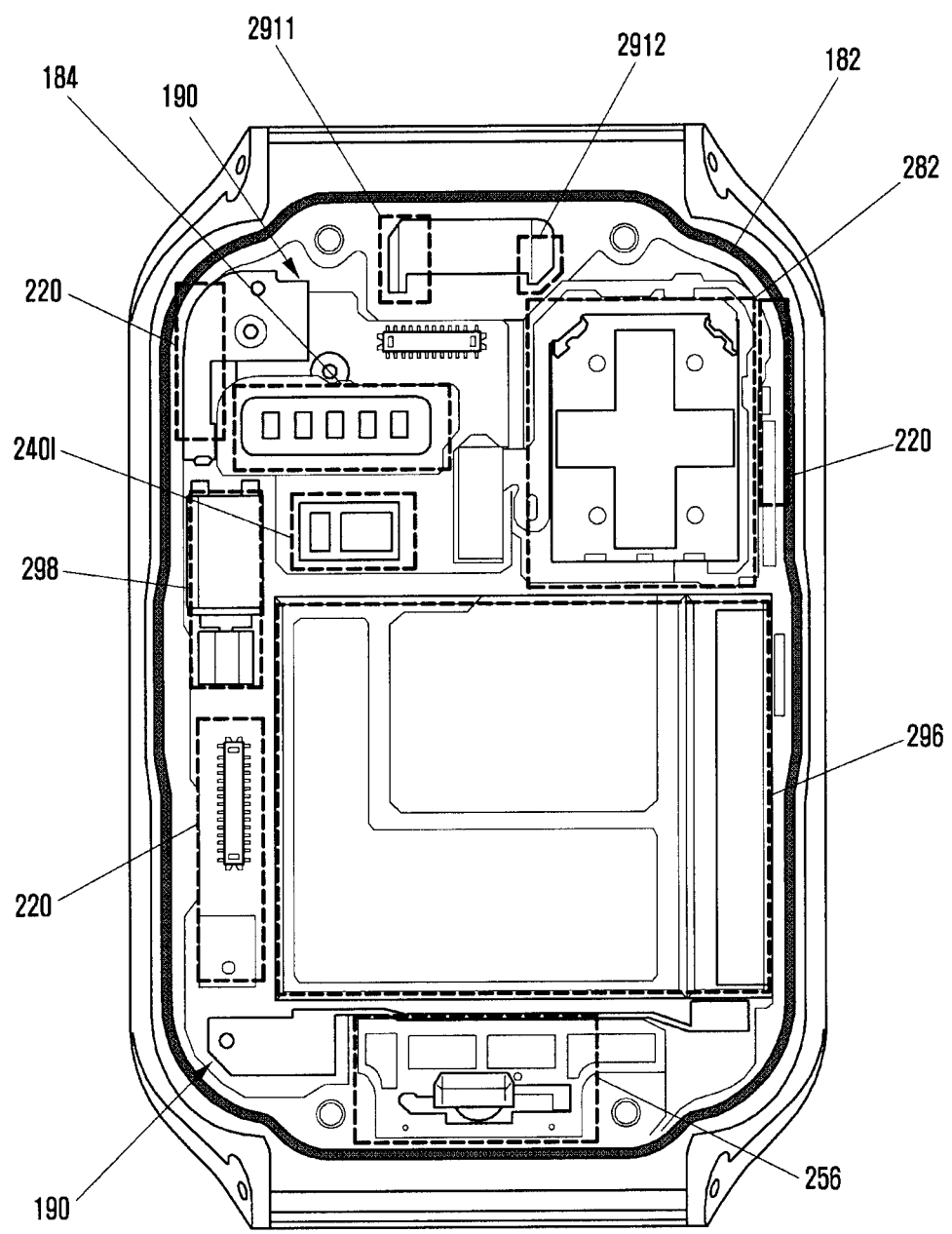
FIG. 9E is a cross-sectional view of the wearable device of FIG. 9A, taken along line V-V of FIG. 9A.

FIG. 9A is a left side view of a wearable device 200 according to embodiments of the present disclosure. FIG. 9B is a cross-sectional view of the wearable device 200, taken along line III-III of FIG. 9A. FIG. 9C is a view of a speaker 282 according to embodiments of the present disclosure. FIG. 9D is a cross-sectional view of the wearable device 200, taken along line IV-IV of FIG. 9A. FIG. 9E is a cross-sectional view of the wearable device 200, taken along line V-V of FIG. 9A.

As shown in FIG. 9A, the body 101 may include an audio outputting unit 2821. The wearable device 200 may output audio via the audio outputting unit 2821. The audio outputting unit 2821 may be placed in the cover 101B. The body 101 may include the audio outputting unit 2821 on one of the sides (e.g., the left side). The housing 101A is formed, part of which is sloped to the direction to be worn on the human body (e.g., wrist) at the same slope angle as the upper side 180A and lower side 180B, respectively. The housing 101A forms holes 101C and 101D at the both ends, into which pins are inserted to connect the band 102A and 101B to the both ends. In another embodiment of the present disclosure, the body 101 includes: the front, shaped as a rounded square or a rounded rectangle; the back opposite to the front; the upper sides 180A and the lower sides 180B between the front and the back; and the left side and the right side between the front and the back. The body 101 forms the sides by the upper sides 180A, the lower sides 180B, the left side, and the right side, which are between the front and the back. The upper side 180A may form an obtuse angle α with the front of the body 101 and an acute angle β with the back of the body 101. The lower side 180B may form an obtuse angle α with the front of the body 101 and an acute angle β with the back of the body 101. The upper side 180A forms a groove. The camera module 291 may include a lens (or a camera window 2913), disclosed to the outside, in the groove. The key 256 may be positioned at the lower side 180B of the body 101 and may protrude therefrom. The left side and the right side are opposite to each other with respect to the display 260. The upper side 180A and the lower side 180B are opposite to each other with respect to the display 260.

As shown in FIG. 9B, the display 260 may be placed on the front of the housing 101A. The body 101 may include a speaker 282 between the housing 101A and the cover 101B. The speaker 282 may be placed under the display 260 and above the cover 101B. The body 101 may include a sealant 182 between the housing 101A and the cover 101B. The sealant 182 prevents containments such as water from infiltrating. For example, the sealant 182 may be a rubber or a water-proof film. The sealant 182 encloses the wearable device 200 so that the enclosed inside space of the wearable device 200 can serve as a back volume for the speaker 282.

As shown in FIG. 9C, the speaker 282 may be designed in such a way that the back side is open so that it can prevent the interference with sound created in the back side of the diaphragm 2822 and the sound of the back side can be transferred inside the wearable device 200.

As shown in FIG. 9D, the display 260 may be placed on the front of the housing 101A. The body 101 may include a speaker 282 or a printed circuit board assembly 190 between the housing 101A and the cover 101B. The speaker 282 or printed circuit board assembly 190 may be placed under the display 260 and close to the cover 101B. The body 101 may further include a buffering member 183 for protecting the display 260 against impacts between the speaker 282 or printed circuit board assembly 190 and the housing 101A. The body 101 may also include a sealant 182 between the housing 101A and the cover 101B. The sealant 182 prevents containments such as water from infiltrating. For example, when viewing from the front of the display 260, the speaker 282 may be placed inside at the top left of the wearable device 200 and the printed circuit board assembly 190 may be placed inside at the top right of the wearable device 200.

As shown in FIG. 9E, the wearable device 200 shows the back by removing the cover 101B. The wearable device 200 may be configured in such a way that a key 256 is placed inside at the bottom and a battery 296 is placed at the top of the key 256. The wearable device 200 may be configured in such a way that a key 256 and a battery 296 are placed inside at the bottom. The wearable device 200 may be configured in such a way that the speaker 282 and the printed circuit board assembly 190 are placed side by side on the battery 296 and the image sensor unit 2911 and the infra-red LED 2912 are placed side by side on the speaker 282 and the printed circuit board assembly 190. For example, when viewing the back of the wearable device 200, the speaker 282 may be placed at the right and the printed circuit board assembly 190 may be placed at the right. For example, when viewing the back of the wearable device 200, the infra-red transceiver 2912 may be placed at the right and the image sensor unit 2911 may be placed at the left.

The printed circuit board assembly 190 may include a connector 184 and a biometric sensor 240I. The wearable device 200 may be configured in such a way that a communication module 220 or a motor 298 are placed at the right and left edges inside the sealant 182. The wearable device 200 may electrically connect to external devices through the connector 184 and may obtain a user's biometric information through the biometric sensor 240I.

Figure 10A:
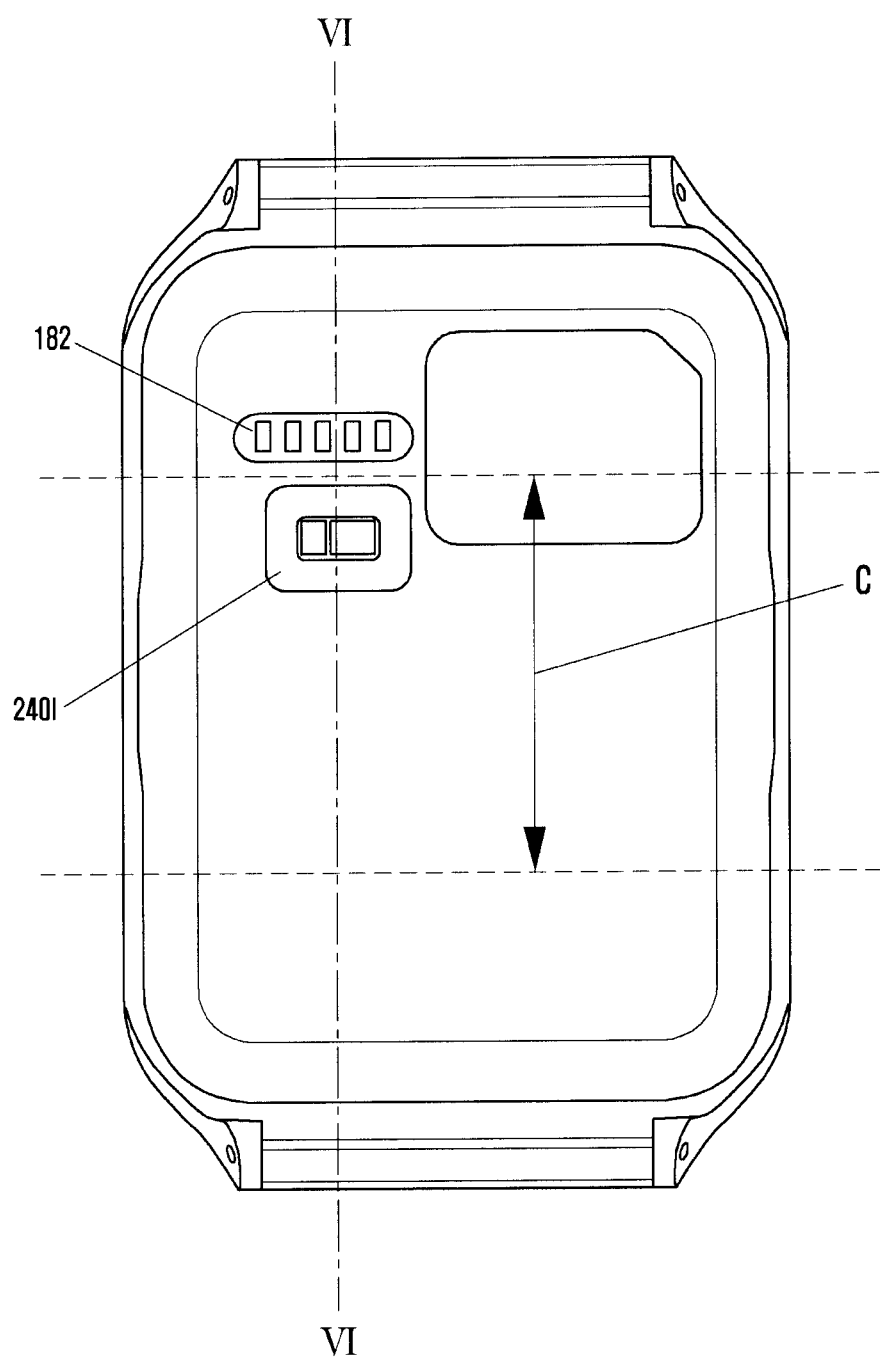
FIG. 10A is a rear view of a wearable device according to embodiments of the present disclosure.
Figure 10B:
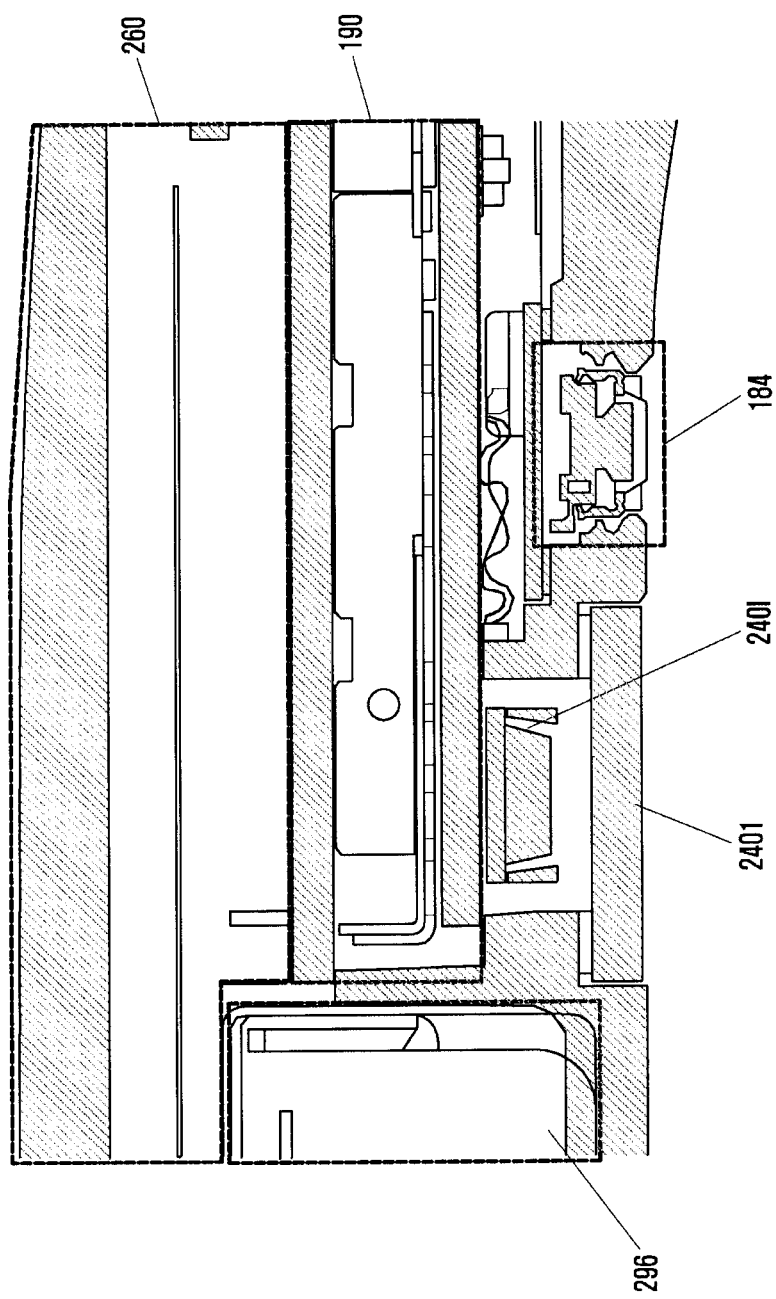
FIG. 10B is a cross-sectional view of the wearable device of FIG. 10A, taken along line VI-VI of FIG. 10A.
Figure 10C:
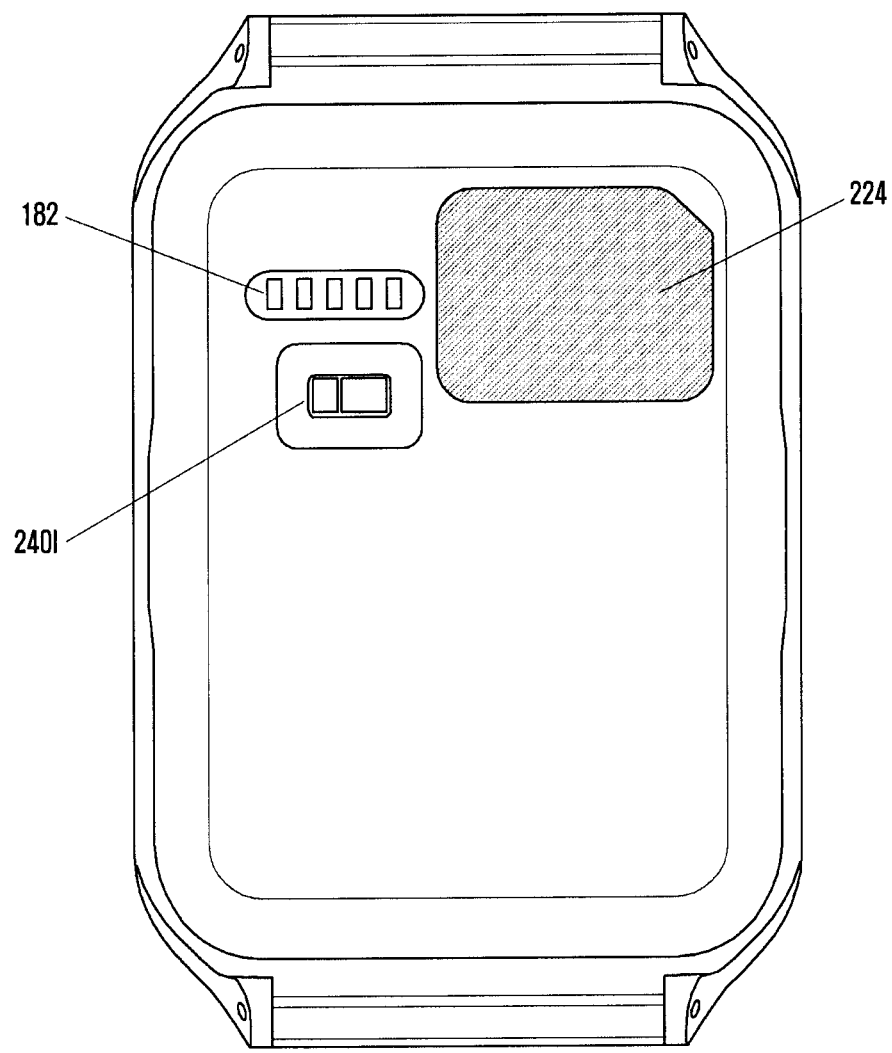
FIG. 10C is a rear view of a wearable device according to embodiments of the present disclosure.
Figure 10D:
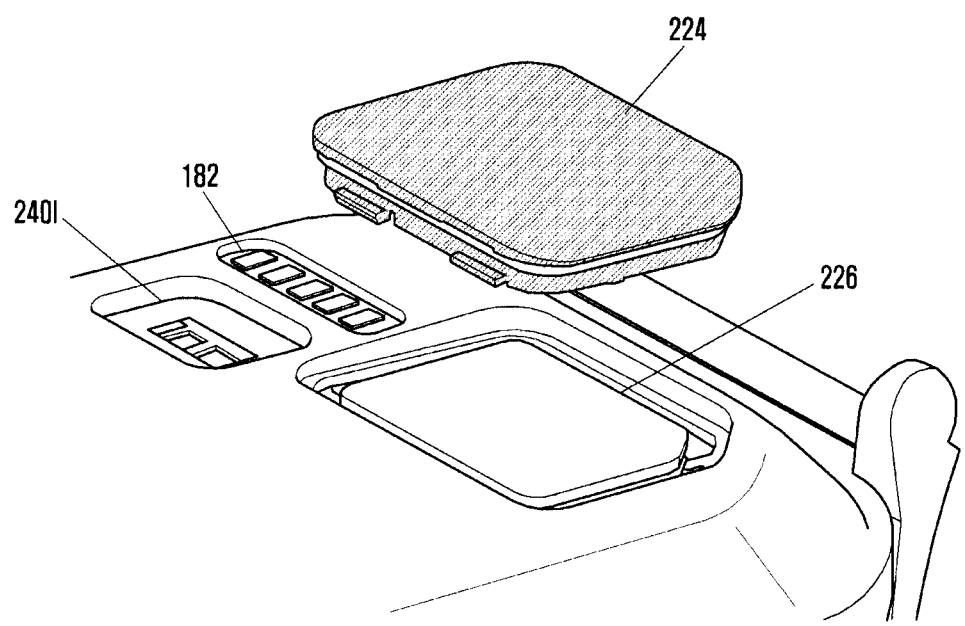
FIG. 10D is a perspective rear view of a wearable device according to embodiments of the present disclosure.

FIG. 10A is a rear view of a wearable device 200 according to embodiments of the present disclosure. FIG. 10B is a cross-sectional view of the wearable device 200, taken along line VI-VI of FIG. 10A. FIG. 10C is a rear side view of a wearable device 200 according to embodiments of the present disclosure. FIG. 10D is a perspective rear view of a wearable device 200 according to embodiments of the present disclosure.

As shown in FIG. 10A, the wearable device 200 may include a connector 184 and a biometric sensor 240I on the back. For example, the biometric sensor 240I may be a hear rate monitor (HRM) sensor. The HRM sensor 240I-1 detects infra-red dispersed from the blood vessels in the wrist of the user wearing the wearable device 200 and measures the user's heart rate. It is preferable that the HRM sensor 240I-1 may be located within the middle C of the three areas into which the body 101 may equally divided in the longitudinal direction (i.e., an area between ⅓ and ⅔ from the top of the body 101). When the HRM sensor 240I-1 is located within an area between ⅓ and ⅔ from the top of the body 101, it may reduce the possibility the HRM sensor 240I-1 to miss the user's wrist, so that it can obtain the accurate heart rate. When viewing the back of the wearable device 200, the HRM sensor 240I-1 is located in the middle C of the three areas into which the body 101 may be equally divided in the longitudinal direction. The connector 184 may be close to the HRM sensor 240I-1 and above the HRM sensor 240I-1. The biometric sensor 240I may further include other types of sensors for sensing biometric information other than the heart rate by the HRM sensor 240I-1, e.g., a sensor for sensing human body. In that case, the sensor for sensing human body or the HRM sensor 240I-1 may be located in the middle A of the three areas into which the body 101 may equally divided in the longitudinal direction. In another embodiment of the present disclosure, the biometric sensor 240I may be located in an area of the body 101 between the first and second virtual lines (as shown in FIG. 10A) apart from ⅓ and ⅔ of the length of the body 101 from the upper side 180A, (i.e., the middle C) expanding parallel to the lengthwise direction of the upper side 180A or the lower side 180B.

As shown in FIG. 10B, the wearable device 200 includes the connector 184 or a window 240I for the HRM sensor on the back. The HRM sensor 240I-1 may be layered on the HRM sensor window 240I. The printed circuit board assembly 190 may be layered on the HRM sensor 240I-1 or the connector 184. The display 260 may be placed above the printed circuit board assembly 190. The HRM sensor window 240I may be made of plastic or toughened glass. The HRM sensor window 240I may form a transparent area corresponding to the area of the HRM sensor 240I-1, through which the HRM sensor 240I-1 may illuminate infra-red and receive the dispersed infra-red from the user.

As shown in FIG. 10C, the wearable device 200 may install an external card 224 (e.g., SIM card, memory card, etc.) in the top of the back. For example, when viewing the back of the wearable device 200, the wearable device 200 may place the connector 184 and the HRM sensor 240I-1 at the left of the back and the external card 224 at the right of the back.

As shown in FIG. 10D, when viewing the rear side of the wearable device 200, the wearable device 200 may place an interface unit 226 receiving the external card 224 at the top right of the back.

Figure 11:
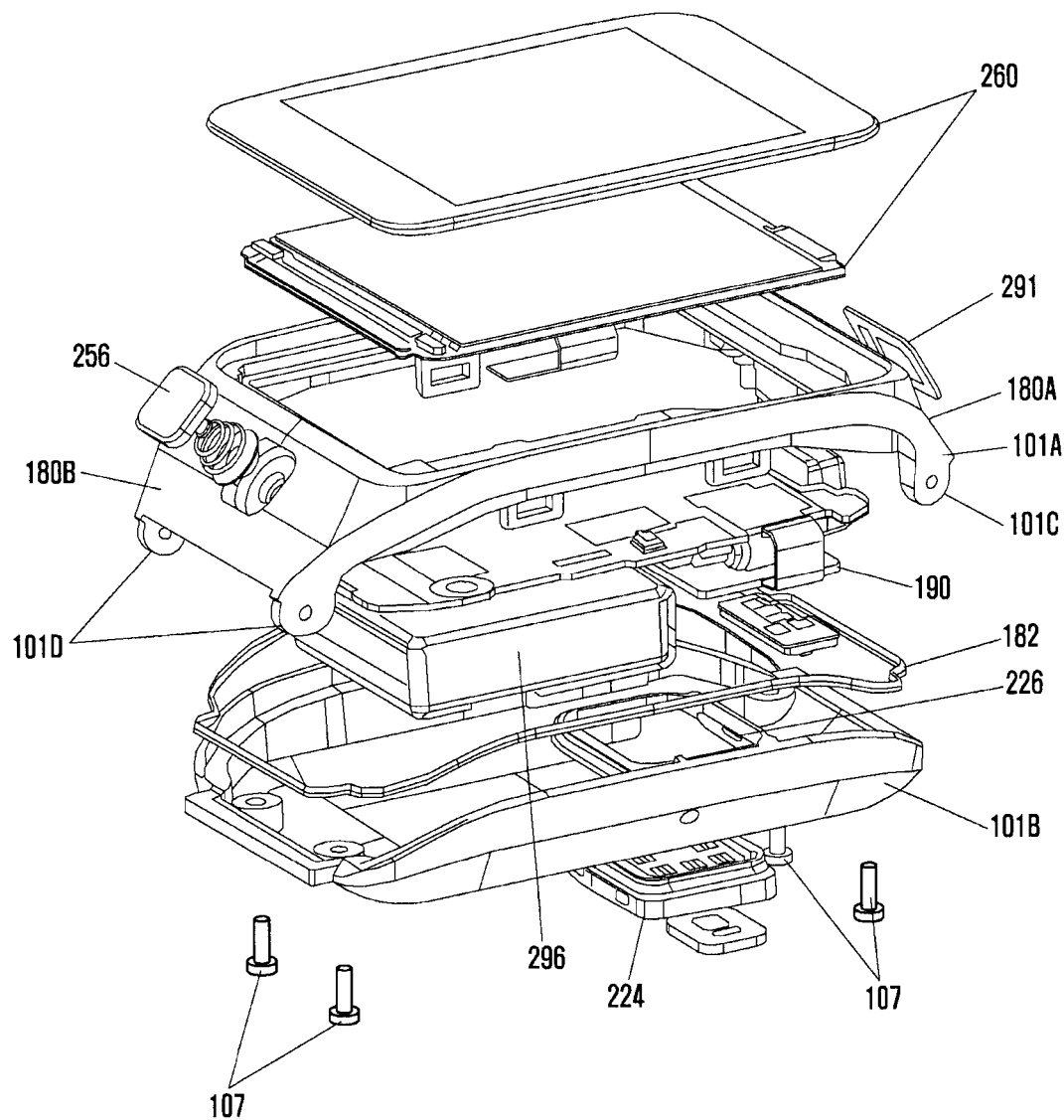
FIG. 11 is an exploded perspective view of a wearable device according to embodiments of the present disclosure.

FIG. 11 is an exploded perspective view of a wearable device according to embodiments of the present disclosure.

The housing 101A includes the display 260 on the front. The housing 101A may be formed to have part of which that may be sloped to the direction to be worn on the human body (e.g., wrist) at the same slope angle as the upper side 180A and lower side 180B, respectively. The housing 101A forms the upper side 180A and lower side 180B, part of which are sloped to the direction to be worn on the human body (e.g., wrist). The camera module 291 may be placed in the center of the upper side 180A. The key 256 may be placed in the center of the lower side 180B. The housing 101A forms holes 101C and 101D at the both ends, into which pins are inserted to connect the band 102A and 101B to the both ends. The first hole 101C may be coupled to the upper band 102A. The second hole 101D is coupled to the lower band 102B. Although the embodiments of the present disclosure describe the band 102 as a dedicated product for the wearable device 200, it should be understood that the wearable device 200 may also employ conventional wrist-watch bands. The cover 101B includes an interface unit 226 (e.g., slots) for receiving the external card 224 (e.g., SIM card or memory card). The body 101 includes: a housing 101A forming the front, the upper 180A and lower 180B sides and one part of the left and right sides; and a cover 101B forming the back, and the other part of the left and right sides (e.g., part of the left and right side included in the housing 101A and part of the left and right sides not included in other housing 101A).

The cover 101B may allow for the arrangement of locking grooves 181A and 181B at both sides to be coupled with an external electronic device (e.g., a charger 300). The cover 101B may allow for the arrangement of the audio outputting unit 2821 to output sound from the side. In another embodiment of the present disclosure, the body 101 may include the audio outputting unit 2821 in the upper side, lower side, left side, right side, or back. The housing 101A and the cover 101B form the body 101 and are coupled to each other by coupling members 107 (e.g., screws). The cover 101B forms coupling holes at the four corners for receiving the coupling members 107 or screws. The housing 101A and the cover 101B may form the body 101 and may include the battery 296 and the printed circuit board assembly 190 in the space therebetween. The housing 101A and the cover 101B are may be coupled to each other and may be enclosed by the sealant 182.

As described above, the wearable devices according to the embodiments of the present disclosure can be configured to include various types of apparatuses and provide a variety of functions to users.

Although exemplary embodiments of the disclosure have been described in detail above, it should be understood that many variations and modifications of the basic inventive concept herein described, which may be apparent to those skilled in the art, will still fall within the spirit and scope of the exemplary embodiments as defined in the appended claims.

What is claimed is:

1. A wearable device comprising:
  a body including:
    a front having a substantially rectangular shape;
    a back opposite to the front;
    an upper side;
    a lower side; and
    a left side and a right side,
    wherein the upper side, the lower side, left side, and right side are positioned between the front and back and couple the front and back;
  an upper band coupled to the upper side;
  a lower band coupled to the lower side;
  a display located on the front of the body;
  a camera module disposed on the upper side; and
  a key disposed on the lower side, the key being operated by being pressed.

2. The wearable device of claim 1, wherein the upper side forms an obtuse angle with the front and an acute angle with the back.

3. The wearable device of claim 1, wherein:
  the upper side comprises a groove; and
  the camera module comprises a lens disposed within the groove.

4. The wearable device of claim 1, wherein the lower side forms an obtuse angle with the front and an acute angle with the back.

5. The wearable device of claim 1, wherein the key is protrudes from the lower side.

6. The wearable device of claim 1, further comprising:
  a charger detachably coupled to at least part of the right side and the left side.

7. The wearable device of claim 6, wherein the charger comprises:
  a portion contacting at least part of the back of the body.

8. The wearable device of claim 6, wherein:
  the back comprises a first electric connector; and
  the charger comprises a second electric connector for electrically contacting the first electric connector.

9. The wearable device of claim 1, wherein the body further comprises:
  a heart rate monitor (HRM) sensor being positioned on the back.

10. The wearable device of claim 9, wherein the upper side has a length, and wherein the HRM sensor is located in a middle area of the body that includes about ⅓ to ⅔ of the length of the upper side.

11. The wearable device of claim 1, wherein the body comprises:
  an interface unit on the back, the interface unit being configured to detachably receive an external card.

12. The wearable device of claim 1, wherein the camera module comprises:
  a camera window placed in the upper side; and
  an image sensor unit, placed inside the body, for obtaining images from the outside via the camera window.

13. The wearable device of claim 12, further comprising:
  an infra-red transceiver, placed inside the body, for transmitting/receiving infra-red signals to/from an external device via the camera window.

14. The wearable device of claim 1, wherein the body comprises:
  an audio outputting unit in at least one of the upper side, the lower side, the left side and the right side.

15. The wearable device of claim 1, wherein the body comprises:
  a housing that forms the front, the upper side, the lower side, the left side and a first part of the right side;
  a cover that forms the back, the left side and a second part of the right side; and
  a sealant placed between the housing and the cover.

16. The wearable device of claim 1, further comprising:
  at least one hole placed at both ends of the body, to the hole being positioned such that the hole does not block an angle of view of the camera module,
  wherein the at least one hole is coupled to the upper band and the lower band.

17. The wearable device of claim 1, wherein the body further comprises:
  a heart rate monitor (HRM) sensor and a biometric sensor for sensing biometric information, the HRM sensor and the biometric sensor being placed in the back.

18. A wearable device comprising:
  a housing including a front, a back, a first side, a second side, a third side, and a fourth side;
  a wearable tool that is attached to at least part of the housing and worn on part of an object;
  a display included in the front;
  a camera window disposed on the first side; and
  an image sensor unit that is included inside the housing and located adjacent to the camera window,
  wherein the front and the first side form an obtuse angle.

19. The wearable device of claim 18, further comprising:
  an infra-red transceiver that is placed inside the housing and disposed through the camera window.

20. The wearable device of claim 18, wherein:
  the first side and the third side are opposite to each other with respect to the display;
  the second side and the fourth side are opposite to each other with respect to the display; and
  a first angle formed by the front and the first side differs from a second angle formed by the front and the third side.

21. The wearable device of claim 18, further comprising:
a speaker that is placed inside the housing, at least part of the speaker being disposed at least one of the second and fourth sides of the housing.

22. The wearable device of claim 18, further comprising:
a heart rate monitor (HRM) sensor placed in the back of the housing.

23. The wearable device of claim 18, further comprising:
a charging connector placed in the back of the housing.

24. The wearable device of claim 18, further comprising:
a communication module positioned inside the housing.

* * * * *